United States Patent
Puri et al.

(10) Patent No.: US 10,117,942 B2
(45) Date of Patent: Nov. 6, 2018

(54) PHOTOACTIVATABLE LIPID-BASED NANOPARTICLES AS VEHICLES FOR DUAL AGENT DELIVERY

(71) Applicants: The United States of America, as represented by the Secretary, Department of Health and Human Services, Washington, DC (US); Baylor College of Medicine, Houston, TX (US)

(72) Inventors: Anu Puri, Frederick, MD (US); Robert P. Blumenthal, Bethesda, MD (US); Amit Joshi, Houston, TX (US); Darayash B. Tata, Silver Spring, MD (US); Mathias Viard, Frederick, MD (US)

(73) Assignees: The United States of America, as represented by the Secretary, Department of Health and Human Services, Washington, DC (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 14/904,385

(22) PCT Filed: Jul. 9, 2014

(86) PCT No.: PCT/US2014/045922
§ 371 (c)(1),
(2) Date: Jan. 11, 2016

(87) PCT Pub. No.: WO2015/006429
PCT Pub. Date: Jan. 15, 2015

(65) Prior Publication Data
US 2016/0136289 A1    May 19, 2016

Related U.S. Application Data

(60) Provisional application No. 61/845,861, filed on Jul. 12, 2013.

(51) Int. Cl.
| | |
|---|---|
| *A61K 9/00* | (2006.01) |
| *A61K 31/704* | (2006.01) |
| *A61K 9/127* | (2006.01) |
| *A61K 41/00* | (2006.01) |
| *A61N 5/06* | (2006.01) |
| *A61K 47/48* | (2006.01) |
| *A61K 47/54* | (2017.01) |
| *A61K 47/69* | (2017.01) |
| *A61N 5/067* | (2006.01) |

(52) U.S. Cl.
CPC ...... *A61K 47/48069* (2013.01); *A61K 9/0019* (2013.01); *A61K 9/1271* (2013.01); *A61K 31/704* (2013.01); *A61K 41/0042* (2013.01); *A61K 41/0071* (2013.01); *A61K 47/546* (2017.08); *A61K 47/6911* (2017.08); *A61N 5/062* (2013.01); *A61N 2005/067* (2013.01); *A61N 2005/0663* (2013.01)

(58) Field of Classification Search
None
See application file for complete search history.

(56) References Cited

U.S. PATENT DOCUMENTS

| 7,169,753 B2 | 1/2007 | Scheer et al. |
| 7,354,599 B2 | 4/2008 | Albrecht et al. |
| 2010/0056983 A1* | 3/2010 | Dougherty ........... A61N 5/0601 604/20 |

FOREIGN PATENT DOCUMENTS

| WO | WO 2012/006009 A1 | 1/2012 |
| WO | WO 2013/082702 A1 | 6/2013 |

OTHER PUBLICATIONS

Ludmila O. Cinteza, Tymish Y. Ohulchanskyy, Yudhisthira Sahoo, Earl J. Bergey, Ravindra K. Pandey, and Paras N. Prasad. Diacyl-lipid Micelle-Based Nanocarrier for Magnetically Guided Delivery of Drugs in Photodynamic Therapy. Molecular Pharmaceutics, vol. 3, No. 4, 415-423.*
Amichai Yavlovich, Alok Singh, Robert Blumenthal, Anu Puri. A novel class of photo-triggerable liposomes containing DPPC:DC8,9PC as vehicles for delivery of doxorubcin to cells. Biochimica et Biophysica Acta 1808 (2011) 117-126.*
Isabelle Noiseux, Ozzy Mermut, Jean-Pierre Bouchard, Jean-François Cormier, Patrice Desroches, Michel Fortin, Pascal Gallant, Sébastien Leclair, Marcia L. Vernon. Effect of liposomal confinement on photochemical properties of photosensitizers with varying hydrophilicity. Journal of Biomedical Optics 13_4_, 041313 _Jul./Aug. 2008.*
Cinteza, et al., "Diacyllipid Micelle-Based Nanocarrier for Magnetically Guided Delivery of Drugs in Photodynamic Therapy," *Molecular Pharmaceutics*, vol. 3(4):415-423, 2006 (Abstract only).
Colantonio, et al., "Quantitative Analysis of Phospholipids Using Nanostructured Laser Desorption Ionization Targets," *Lipids, Author Manuscript*, vol. 46(5):469-477, 2011.

(Continued)

*Primary Examiner* — Michael P Cohen
(74) *Attorney, Agent, or Firm* — Klarquist Sparkman, LLP

(57) ABSTRACT

Embodiments of photoactivatable, lipid-based nanoparticles are disclosed, as well as methods of making and using the nanoparticles. Pharmaceutical compositions including the nanoparticles also are disclosed. The lipid-based nanoparticles include a vesicle wall surrounding a cavity, wherein the vesicle wall includes (i) a lipid bilayer comprising 1,2-bis(tricosa-10,12-diynoyl)-sn-glycero-3-phosphocholine ($DC_{8,9}PC$), dipalmitoylphosphatidylcholine (DPPC), and (ii) 2-[1-hexyloxyethyl]-2-devinyl pyropheophorbide-a (HPPH) within the lipid bilayer. The nanoparticles may further include an agent within the cavity.

21 Claims, 22 Drawing Sheets

(56) References Cited

OTHER PUBLICATIONS

Gupta, et al., "Multifunctional Nanoplatforms for Fluorescence Imaging and Photodynamic Therapy Developed by Post-Loading Photosensitizer and Fluorophore to Polyacrylamide Nanoparticles," *Nanomedicine: Nanotechnology, Biology, and Medicine*, vol. 8:941-950, 2012.

International Search Report and Written Opinion, dated Oct. 27, 2014, issued in corresponding International Application No. PCT/US2014/045922.

Lamparski, et al., "Photoinduced Destabilization of Liposomes," *Biochemistry*, vol. 31:685-694, 1992.

Mermut, et al., "Effect of Liposomal Confinement on Photothermal and Photo-oximetric Fluorescence Lifetimes of Photo sensitizers with Varying Hydrophilicity," *Journal of Biomedical Optics*, vol. 13(4), 041314-01-11, Jul./Aug. 2008.

Noiseaux, et al., "Effect of Liposomal Confinement on Photochemical Properties of Photosensitizers with Varying Hydrophilicity," *Journal of Biomedical Optics*, vol. 13(4):041313-1-041313-11, Jul./Aug. 2008.

Roy, et al., "Ceramic-Based Nanoparticles Entrapping Water-Insoluble Photosensitizing Anticancer Drugs: A Novel Drug-Carrier System for Photodynamic Therapy," *JACS*, vol. 125:7860-7865, 2003.

Wang, et al., "Novel Methods to Incorporate Photosensitizers into Nanocarriers for Cancer Treatment by Photodynamic Therapy," *Lasers Surg Med, Author Manuscript*, vol. 43(7):686-695, 2011.

Yavlovich, et al. "Design of Liposomes Containing Photopolymerizable Phospholipids for Triggered Release of Contents," *J Therm Anal Calorim, Author Manuscript*, 98(1):97-104, 2009.

Yavlovich, et al., "Light-Sensitive Lipid-Based Nanoparticles for Drug Delivery: Design Principles and Future Considerations for Biological Applications," *J Molecular Membrane Biology, Author Manuscript*, vol. 27(7):364-381, 2010.

Yavlovich, et al., "A Novel Class of Photo-Triggerable Liposomes Containing DPPC:$DC_{8,9}PC$ as Vehicles for Delivery of Doxorubcin to Cells," *Biochimica et Biophysica ACTA (BBA)—Biochimica et Biophysica Acta*, vol. 1808(1):117-126, 2011.

Yavlovich, et al., "Low-Visibility Light-Intensity Laser-Triggered Release of Entrapped Calcein from 1,2-bis (tricosa-10,12-diynoyl)-sn-glycero-3-phosphocholine Liposomes is Mediated through a Type 1 Photoactivation Pathway," *International Journal of Nanomedicine, Author Manuscript*, vol. 8:2575-2587, 2013.

* cited by examiner

HPPH standard curve liposome associated HPPH

Liposome Absorbance Spectra

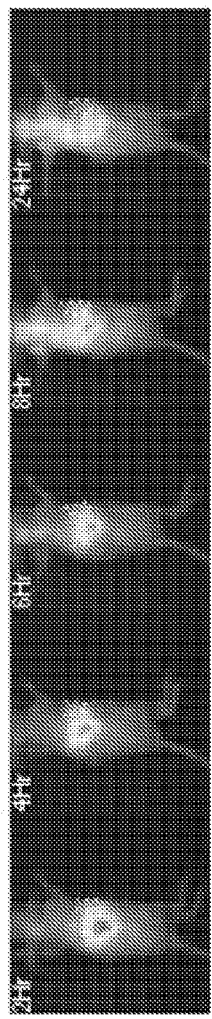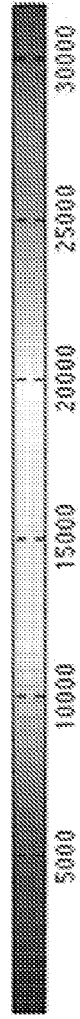
FIG. 18B
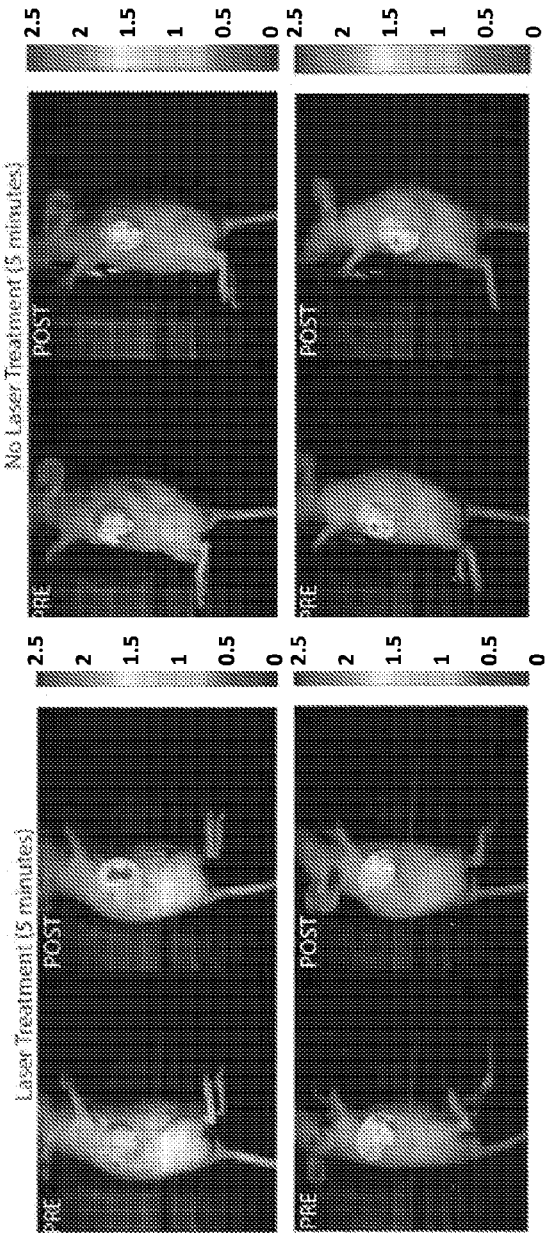
FIG. 19A
Laser Treatment (5 minutes)
FIG. 19C
No Laser Treatment (5 minutes)
FIG. 19B
FIG. 19D

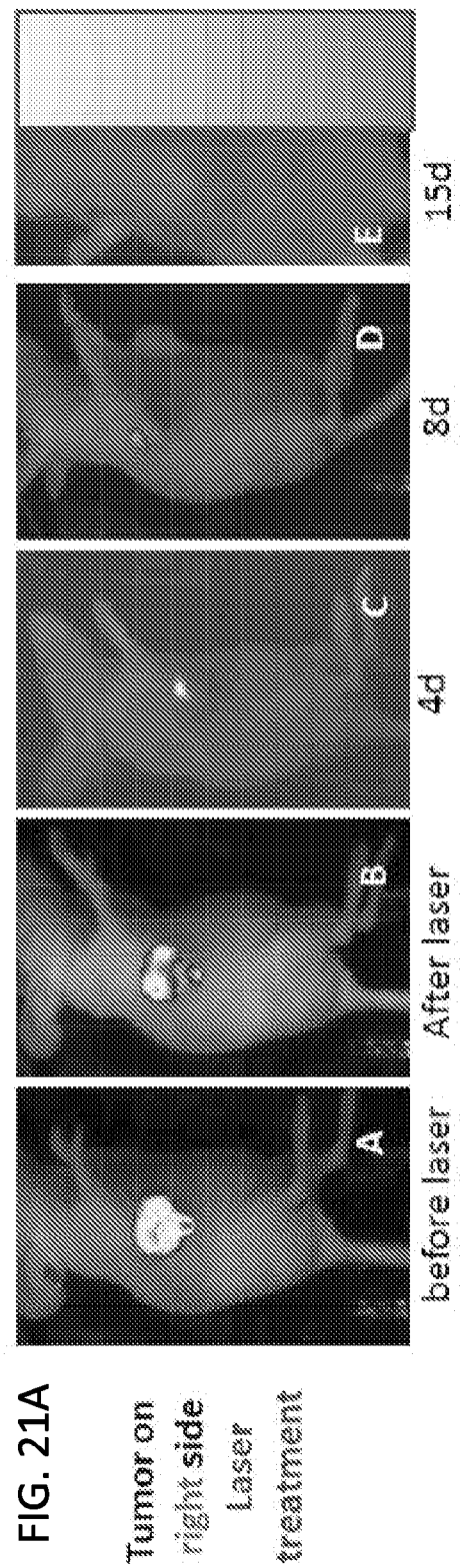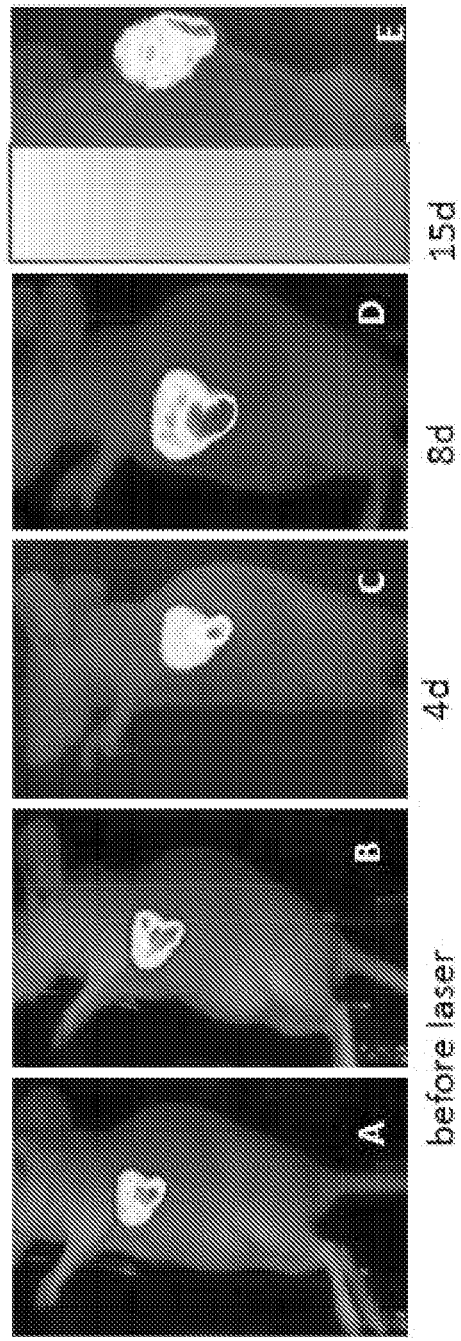
FIG. 21A Tumor on right side Laser treatment
FIG. 21B Tumor on left side NO treatment Tumor on left side Laser treatment Tumor on right side NO treatment FIG. 24
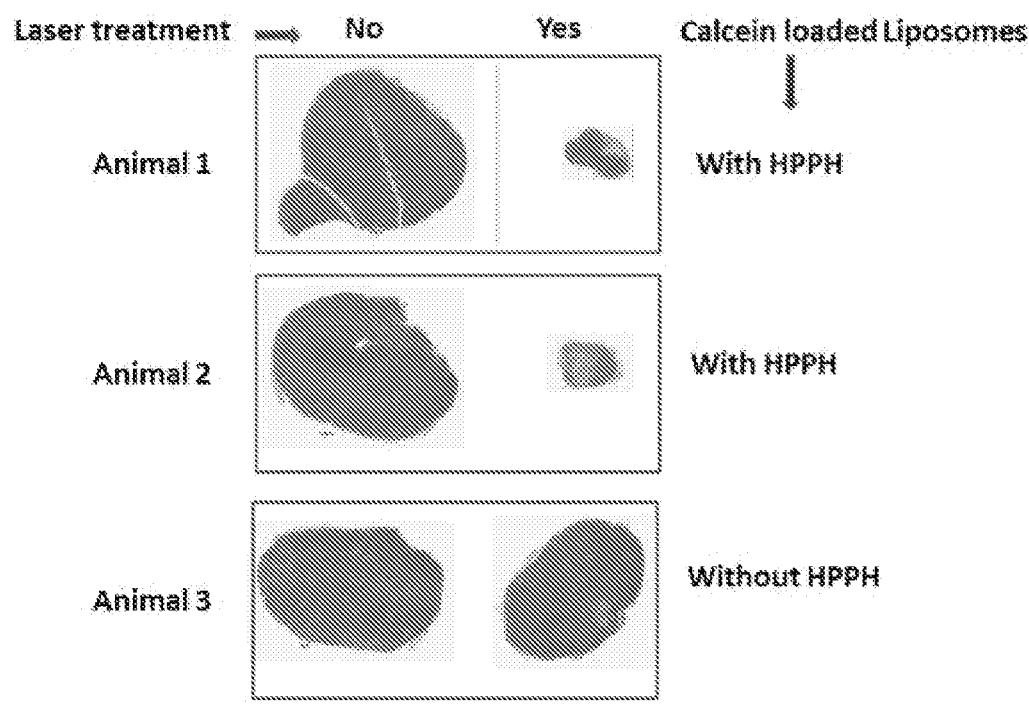
FIG. 25A   FIG. 25B
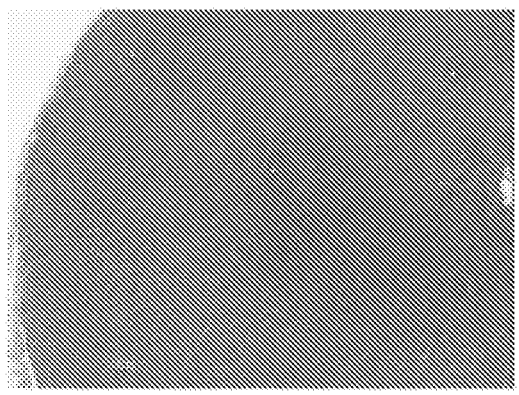 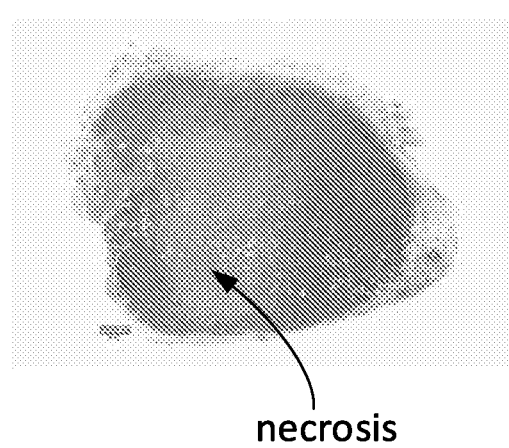
necrosis

PHOTOACTIVATABLE LIPID-BASED NANOPARTICLES AS VEHICLES FOR DUAL AGENT DELIVERY

CROSS REFERENCE TO RELATED APPLICATIONS

This is the U.S. National Stage of International Application No. PCT/US2014/045922, filed Jul. 9, 2014, which was published in English under PCT Article 21(2), which in turn claims the benefit of U.S. Provisional Application No. 61/845,861, filed Jul. 12, 2013, each of which is herein incorporated by reference in its entirety.

FIELD

This disclosure relates generally to liposomes for agent delivery, pharmaceutical compositions comprising the liposomes, and methods for making and using the liposomes.

PARTIES TO JOINT RESEARCH AGREEMENT

The National Cancer Institute, National Institutes of Health, the Food and Drug Administration, and Baylor College of Medicine are parties to a joint research agreement related to the technology disclosed herein.

BACKGROUND

Targeted delivery of anti-cancer agents to tumor tissue, with minimum damage to normal cells and tissue, is an important goal in cancer therapy. Cancer nanotechnology platforms have shown promise. However, an important consideration for effective drug delivery is precise spatial and temporal release of therapeutic agents at the target site. The development of on-demand drug release (triggering) approaches is based on utilization of either abnormal biology of the tumors (internal) or the unique physical properties of the nanoparticles (external trigger). In the liposome field, various triggering modalities used in the past include local hyperthermia, use of metal ions, pH, enzymes and light (radiation) (Torchilin et al., *Nat. Rev. Drug. Discov.* 2005, 4, 145-160; Andresen et al., *Prog. Lipid Res.* 2005, 44, 68-97).

Liposomes include a lipid bilayer wall surrounding a cavity. A molecule, such as a bioactive agent, can be encapsulated within the cavity. If the lipid bilayer is disrupted, the bioactive agent may be released from the cavity. Disruption can occur when a conformational change in one or more lipids in the lipid bilayer is induced, thereby destabilizing the lipid bilayer. One mechanism for disruption is photo-triggering. Light-sensitive liposomes have been studied since the early 1980s. When a light-sensitive liposome is exposed to light, the liposome's lipid bilayer is disrupted and an agent within the liposomal cavity can be released. The principle(s) of photo-triggering include photo-topolymerization of lipids (Regen et al., *Biochem. Biophys. Res. Commun.* 1981, 101, 131-136), photosensitization by membrane anchored hydrophobic probes (Bisby et al., *BBRC* 2000, 276, 169-173; Chandra et al., *Org. Biomol. Chem.* 2006, 4, 1730-1740; Lavi et al., *Biophys. J.* 2002, 82, 2102-2110), or photoisomerization of photoreactive lipids (Morgan et al., *FEBS Lett.* 1995, 375, 113-116). Most photo-triggerable liposomes require ultraviolet light radiation to disrupt the lipid bilayer. Ultraviolet light triggering, however, is unsuitable for in vivo applications since UV light cannot penetrate tissue to a sufficient depth to be effective. Thus, there is a need for liposomes that are responsive to tissue-penetrating wavelengths for "on-demand" drug release in vivo.

SUMMARY

Embodiments of photoactivatable, lipid-based nanoparticles (liposomes) are disclosed, as well as methods of making and using the liposomes. Pharmaceutical compositions comprising the liposomes also are disclosed.

The liposomes include a vesicle wall surrounding a cavity, and the vesicle wall includes (i) a lipid bilayer comprising, for example, 1,2-bis(tricosa-10,12-diynoyl)-sn-glycero-3-phosphocholine ($DC_{8,9}PC$), dipalmitoylphosphatidylcholine (DPPC), and (ii) a tetrapyrollic photosensitizer, such as 2-[1-hexyloxyethyl]-2-devinyl pyropheophorbide-a (HPPH) within the lipid bilayer. The lipid bilayer may include one or more segregated regions, or pockets, of $DC_{8,9}PC$ with the HPPH being preferentially located within the $DC_{8,9}PC$ pockets. The liposomes may further include an agent, such as a pharmaceutical agent, within the cavity. In some embodiments, the lipid bilayer includes from 10 mol % to 20 mol % $DC_{8,9}PC$. The lipid bilayer may have a lipid:HPPH weight ratio from 80:1 to 10:1. In some embodiments, the lipid bilayer further includes a stabilizing lipid including surface-bound polyethylene glycol (PEG). An exemplary stabilizing lipid is 1,2-distearoyl-sn-glycero-3-phosphoethanolamine-N-methoxy(polyethylene glycol) (DSPE-PEG), such as from 3 mol % to 5 mol % DSPE-PEG.

The liposome may further include at least one agent within the cavity. The agent may be an anti-cancer agent, an imaging agent, an anti-inflammatory agent, or a nucleic acid molecule, such as an siRNA molecule.

Embodiments of pharmaceutical compositions include a liposome as described herein and a pharmaceutically acceptable carrier.

A method for dual delivery of HPPH and an agent from a photoactivatable lipid-based nanoparticle includes providing a liposome as disclosed herein, and irradiating the liposome with targeted application of light having a wavelength in the near-infrared range and a selected intensity for an effective period of time to activate at least a portion of the HPPH and release at least a portion of the agent from the cavity of the liposome. In some embodiments, the light is a laser that produces light with a wavelength of 650-670 nm, such as a 660 nm laser. The selected intensity may be from 1 mW to 500 mW. The effective period of time may be at least 30 seconds.

In some embodiments, the agent is a bioactive agent, and the method further includes identifying a subject as having a condition that may be treated with HPPH, the bioactive agent, or both HPPH and the bioactive agent, administering the photoactivatable liposome (or a pharmaceutical composition comprising the photoactivatable liposome) to the subject, and irradiating the photoactivatable liposome by targeted application of light having a selected wavelength in the near-infrared range and a selected intensity to a targeted portion of the subject for the effective period of time. The subject may have, for example, a tumor and the portion of the subject includes an area proximate a location of the tumor. Administering the photoactivatable liposome to the subject may include administering an amount of the photoactivatable liposome effective to induce tumor size regression. The photoactivatable liposome may be administered to the subject by intravenous injection. Irradiation may be performed 4-6 hours after administering the photoactivatable liposome to the subject. Irradiating the liposome by targeted application of light can be performed by externally applying the light to the targeted portion of the subject for the effective period of time, thereby transcutaneously applying the light to the tumor. Alternatively, the light may be internally applied, such as by using an endoscope or a fiber optic catheter.

A method for impairing growth of a tumor in a subject includes administering to the subject a therapeutically effective amount of a photoactivatable liposome as disclosed herein, and subsequently irradiating the photoactivatable liposome by targeted application of light having a selected wavelength in the near-infrared range and a selected intensity to an area of the subject proximate a location of the tumor for an effective period of time, thereby impairing growth of the tumor. In some embodiments, the effective period of time is at least 30 seconds. The light can be applied externally or internally as described above. Irradiating may be performed 4-6 hours after administering the photoactivatable liposome to the subject. The photoactivatable liposome may be administered to the subject by intravenous injection.

The foregoing and other objects, features, and advantages of the invention will become more apparent from the following detailed description, which proceeds with reference to the accompanying figures.

BRIEF DESCRIPTION OF THE DRAWINGS

FIG. 18B is a series of representative images of DiR fluorescence illustrating the time-dependent accumulation of liposomes (Formulation V) in mouse tumors. The tumor ROI is outlined with white circles.

FIGS. 19A-19D are a series of fluorescence images showing calcein release from liposomes including HPPH upon 660 nm laser treatment (5 minutes) of xenografts in mice. Laser treatment was performed four hours after intravenous injection of the liposomes. The calcein fluorescence images in the tumor regions are overlaid on white light images of the mice for spatial registration. Images were normalized with the average pre-laser treatment calcein fluorescence intensity in the tumor ROI. FIGS. 19A and 19B show the calcein release before and after laser treatment of HPPH-DPPC-$DC_{8,9}$PC-calcein liposomes (Formulation V) (19A) and DPPC-$DC_{8,9}$PC-calcein liposomes (Formulation VI) (19B). FIGS. 19C and 19D show the fluorescence in the absence of laser treatment of HPPH-DPPC-$DC_{8,9}$PC-calcein liposomes (Formulation V) (19C) and DPPC-$DC_{8,9}$PC-calcein liposomes (Formulation VI) (19D). Formulations V and VI contained 4 mol % DSPE-PEG2000.

FIGS. 21A and 21B are a series of bioluminescent images of luciferin expression in tumors in a mouse injected with HPPH-DPPC-$DC_{8,9}$PC-calcein liposomes (Formulation V). Images were obtained pre-treatment and post-treatment at 0 days, 4 days, 8 days, and 15 days. The tumor on the mouse's right side was treated with a laser (21A); the tumor on the mouse's left side was not treated with the laser (21B). The images at 0 days, 4 days, and 8 days are side views. The images at 15 days are ventral views to show both tumors (treated vs. untreated).

FIG. 24 is a series of color photographs of stained xenograft tumor sections after injection with HPPH-DPPC-$DC_{8,9}$PC-calcein liposomes (Formulation V) (animals 1 and 2) or DPPC-$DC_{8,9}$PC-calcein liposomes (Formulation VI) (animal 3) and laser treatment for 5 minutes. Mice were sacrificed 15 days after the laser treatment, and the tumor tissue was preserved for histological analysis.

FIGS. 25A and 25B are color photographs of stained xenograft tumor sections after injection with HPPH-DPPC-$DC_{8,9}$PC-calcein liposomes (Formulation V) and laser treatment. The image in FIG. 25A was obtained at low magnification. The image in FIG. 25B was taken at higher magnification, and shows evidence of necrosis.

DETAILED DESCRIPTION

Figure 1:
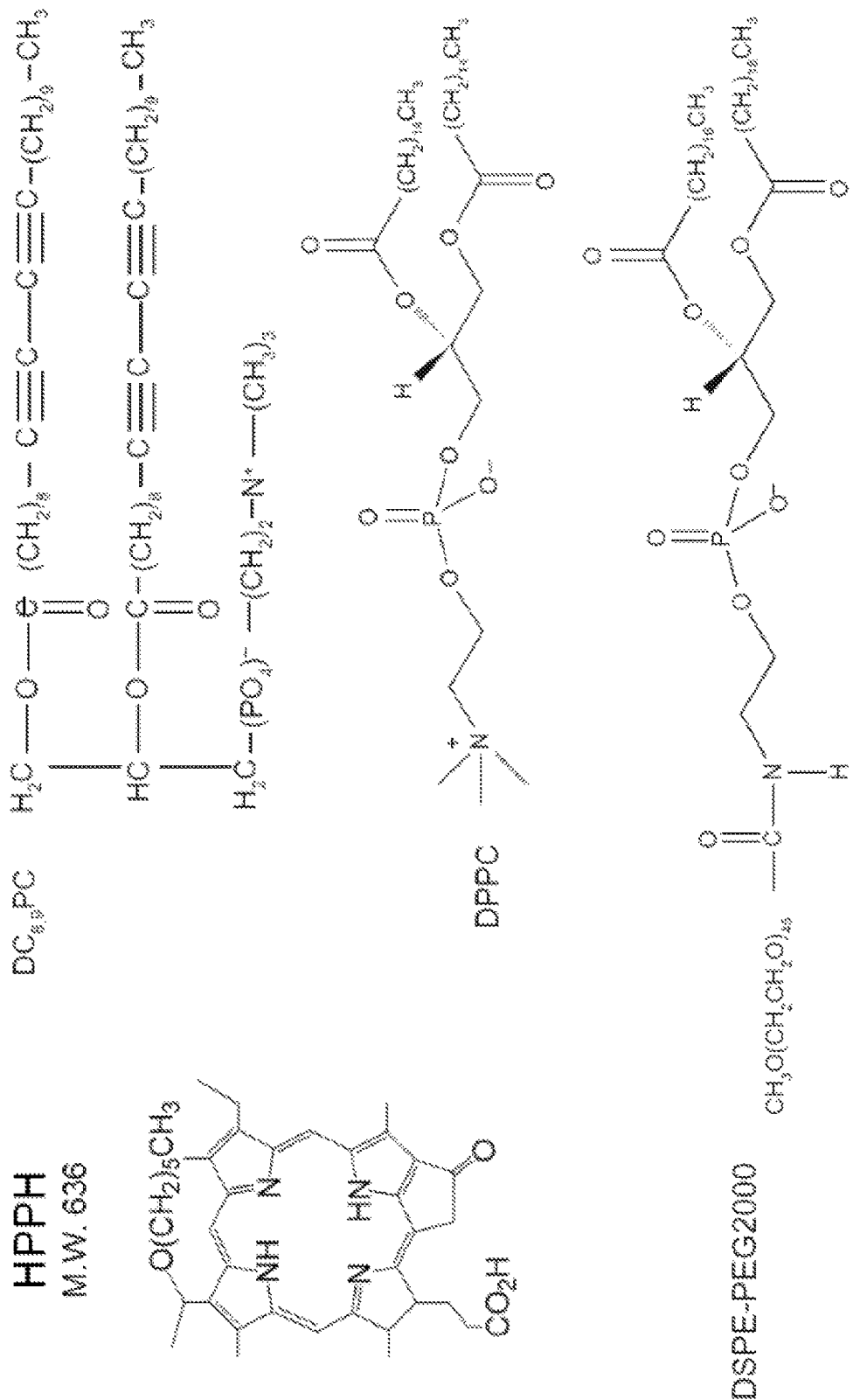
FIG. 1 provides chemical structures of 2-[1-hexyloxyethyl]-2-devinyl pyropheophorbide-a (HPPH), 1,2-bis(tricosa-10,12-diynoyl)-sn-glycero-3-phosphocholine ($DC_{8,9}PC$), dipalmitoylphosphatidylcholine (DPPC), and distearoylphosphatidylethanolamine-polyethylene glycol (DSPE-PEG).

This disclosure concerns embodiments of agent-loaded, lipid-based nanoparticles (liposomes) capable of agent (e.g., drug) release following near-infrared (NIR) light-induced photo-triggering, as well as methods of making and using the liposomes. NIR photo-triggering is advantageous for in vivo applications because NIR energy penetrates tissue to a greater depth (e.g., to several centimeters) than light with shorter wavelengths, such as ultraviolet light. Embodiments of the disclosed liposomes include 1,2-bis(tricosa-10,12-diynoyl)-sn-glycero-3-phosphocholine ($DC_{8,9}$PC), dipalmitoyl phosphatidylcholine (DPPC) and a NIR-sensitive anti-cancer drug, 2-[1-hexyloxyethyl]-2-devinyl pyropheophorbide-a (HPPH, Ex/Em 410/670 nm). Photoactivation (e.g., with a 660 nm laser) releases an agent from the liposome's cavity.

I. Definitions and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Abbreviations:

$DC_{8,9}$PC: 1,2-bis(tricosa-10,12-diynoyl)-sn-glycero-3-phosphocholine

DiR: 1,1'-dioctadecyltetramethyl indotricarbocyanine iodide

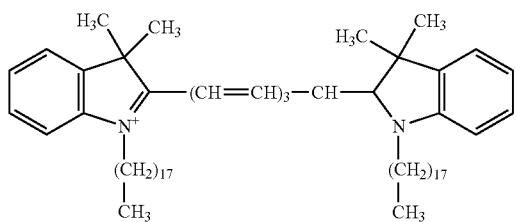

DOPC: 1,2-dioleoyl-sn-glycero-3-phosphocholine (or dioleoyl phosphatidylcholine)

DPPC: 1,2-dipalmitoyl-sn-glycero-3-phosphocholine (or dipalmitoyl phosphatidylcholine)

DSPE-PEG2000 (18:0 PEG2 PE) 1,2-distearoyl-sn-glycero-3-phosphoethanolamine-N-[methoxy(polyethylene glycol)-2000] (ammonium salt)

HBS: HEPES-buffered saline (10 mM HEPES (N-2-hydroxyethylpiperazine-N'-2-ethanesulfonic acid), 140 mM NaCl, pH 7.4-7.5)

HPPH: 2-[1-hexyloxyethyl]-2-devinyl pyropheophorbide-a

NIR: near infrared

PDT: photodynamic therapy

POPC: 1-palmitoyl-2-oleoyl-sn-glycero-3-phosphocholine (or palmitoyl oleoyl phosphatidylcholine)

ROI: region of interest

Explanations of Terms:

The following explanations of terms are provided to better delineate the subject matter of the present disclosure and to guide those of ordinary skill in the art in its practice.

All chemical compounds include either or both of the (+) and (−) stereoisomers, as well as any geometric isomers, such as Z and E isomers and cis and trans isomers. Other chemistry terms herein are used according to conventional usage in the art, as exemplified by *Hawley's Condensed Chemical Dictionary*, Richard J. Lewis, Sr. (ed.), published by John Wiley & Sons, Inc., 1997 (ISBN 0-471-29205-2).

Administering: Administration by any route, for example oral, topical, intravenous, intraperitoneal, intramuscular, intralesional, intranasal, or subcutaneous administration, release from a suppository, or the implantation of a slow-release device (e.g., a mini-osmotic pump) to the subject. "Parenteral" administration is by any route other than through the alimentary tract and includes intravascular administration directly into a blood vessel, for example by intravenous or intra-arterial administration.

Lipid: An inclusive term for fats and fat-derived materials. Lipids include esters of fatty acids (simple lipids, such as fats, sterols, waxes, and triglycerides) or closely related substances (compound lipids, such as phospholipids). Lipids generally are insoluble in water but soluble in organic solvents.

Liposome: A lipid bilayer vesicle that encloses a cavity. The cavity within the liposome is a closed internal space, capable of encapsulating an agent, such as a drug for targeted delivery to a target site within the body. Liposomes may be characterized by membrane type. Unilamellar vesicles have a single membrane. Oligolamellar vesicles and multilamellar vesicles have multiple, usually concentric, membrane layers and are typically larger than 0.1 µm. Liposomes with several nonconcentric membranes, i.e., several small vesicles contained within a larger vesicle, are termed multivesicular vesicles. Conventional liposomes are formulated to carry therapeutic agents, drugs or other active agents either contained within the aqueous interior space (water soluble active agents) or partitioned into the lipid bilayer (water-insoluble active agents). Embodiments of the disclosed liposomes are "unilamellar," i.e., the liposomes have a single lipid bilayer membrane.

Liposome-forming lipid: Any lipid that is capable of forming liposomes. Typically, the "liposome-forming lipid" is a lipid that can form lipid bilayers. Examples of liposome-forming lipids include phospholipids, glycolipids and sphingolipids. The phospholipids that are liposome-forming include phosphatidylcholine, phosphatidylserine, phosphatidylinositol, phosphatidylglycerol, diphosphatidylglycerol and N-acyl phosphatidylethanolamine. In some embodiments, the phospholipid is a phosphatidylcholine or a phosphatidylethanolamine.

Nanoparticle: A nanoscale particle with a size that is measured in nanometers. As used herein, the term nanoparticle refers to a particle having one or more dimensions of 200 nm or less.

Near infrared (NIR): A region of the electromagnetic spectrum between the visible region and the infrared region. There is no set definition for the boundaries of the near-infrared region, but definitions include the wavelength ranges from 650-2500 nm, 750-2500 nm, 780-2500 nm, 800-2500 nm, 700-1400 nm, or 780-3000 nm. As used herein, NIR refers to the wavelength region of 650-2500 nm.

Nucleic acid molecule: Includes DNA and RNA. The DNA may be operably linked to a promoter and/or contained with an expression vector, such as a plasmid. The DNA may be genomic (with introns) or consist only of the intron-less cDNA coding sequence. In some examples, the DNA sequence may encode a therapeutic protein, such as an anti-tumor protein. In other examples, the RNA sequence may be an inhibitory RNA (iRNA) that inhibits gene expression. Examples include microRNA (miRNA) and small interfering RNA (siRNA).

Partition coefficient: A solubility ratio of the non-ionized form of an ionizable compound between two immiscible phases, e.g., an organic solvent and water. The water is adjusted to a pH at which the compound is in its non-ionized form. Generally, the partition coefficient is expressed as a logarithmic term, where log P is defined as the logarithm of the solute concentration in 1-octanol over the solute concentration in water. Log P is a measure of a compound's lipophilicity.

PEGylation: With respect to liposomes, PEGylation refers to incorporating surface-bound polyethylene glycol (PEG) to protect liposomes from detection by the reticuloendothelial system and to increase blood circulation time of the liposome. Polyethylene glycols (PEG) are hydrophilic polymers composed of repeating ethylene oxide subunits with two terminal hydroxyl groups that can be chemically activated. The general structure of PEG is: OH—$(CH_2CH_2O)_n$—$CH_2CH_2$—OH. PEG chains can be linear or branched. PEG conjugation to a pharmaceutically or biologically useful agent requires activating the PEG by preparing a PEG derivative having functional groups. The functional group on PEG is chosen based on the reactive group of the molecule to be conjugated. The molecular weight of the PEGs is chosen to avoid rapid clearance by the liver as well as any toxic effects. Generally, PEG with molecular weight>1000 Da is non-toxic in vivo. PEG with molecular weights of or up to 20,000-50,000 Da have been found to be effective and are generally used in clinical and approved pharmaceutical applications.

Pharmaceutical or bioactive agent: A molecule that is capable of providing a therapeutic (including diagnostic) effect. A bioactive agent has an effect on living tissue.

Examples include anti-cancer agents, imaging agents, anti-inflammatory agents, and small interfering RNA (siRNA) molecules.

Pharmaceutically acceptable: The term "pharmaceutically acceptable" refers to substance that can be taken into a subject without significant adverse toxicological effects on the subject.

Pharmaceutically acceptable carriers: Conventional pharmaceutically acceptable carriers are useful for practicing the methods and forming the compositions disclosed herein. *Remington's Pharmaceutical Sciences*, by E. W. Martin, Mack Publishing Co., Easton, Pa., 15th Edition, 1975, describes examples of compositions and formulations suitable for pharmaceutical delivery of the liposomes herein disclosed.

In general, the nature of the carrier will depend on the particular mode of administration being employed. For example, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phospholipid: A lipid that includes a phosphate group. The phospholipid comprises a glycerol bound to the phosphate group and two fatty acid chains.

Photoactivatable/Photo-triggerable: Capable of being activated (e.g., converted from an inert form to an active form) by light energy.

Photoactivation/Photo-triggering: Activating a liposome using light energy. As used herein, activating means destabilizing the liposome's lipid bilayer wall so that at least a portion of an agent within the liposome's cavity is released. In some embodiments, photoactivation occurs upon exposure of the liposome to a photoactivator, such as targeted application of light of a selected wavelength, intensity, and/or surface area, to a pre-selected target area. In specific non-limiting examples, the light has an intensity of 1 mW to 500 mW (e.g., 0.0005 $W/cm^2$ to 5 $W/cm^2$) and is applied for a sufficient period of time to release an effective amount of a pharmaceutical agent from the liposome. In some examples, a 660 nm, 90 mW laser was used for external, transcutaneous photoactivation. Intensities at the lower end of the range may be used for intravascular and/or endoscopic photoactivation.

Photosensitizer: A molecular or atomic species that initiates a photochemical reaction. The term "photosensitizer" also refers to a substance that sensitizes an organism, cell, or tissue to light. Photosensitizers may be used, for example, in photodynamic therapy for treatment of cancer. The photosensitizer absorbs light of a particular wavelength or wavelength range and becomes excited. The excited photosensitizer transfers energy to nearby molecules. In photodynamic therapy, the photosensitizer may be taken up by a cancer cell. Upon light absorption, the photosensitizer transfers energy to oxygen present within the cell, thereby producing reactive oxygen species which are toxic to cancer cells.

Subject: An animal or human subjected to a treatment, observation or experiment.

Therapeutically effective amount: A quantity or concentration of a specified compound or composition sufficient to achieve a desired effect in a subject being treated. For example, this may be the amount of a photoactivatable lipid-based nanoparticle as disclosed herein, or pharmaceutical composition comprising the photoactivatable lipid-based nanoparticle, necessary to cause tumor cell death or inhibition, thereby eliminating a tumor, reducing the size of a tumor, and/or inhibiting tumor growth in a subject. Ideally, a therapeutically effective amount of a compound or composition is an amount sufficient to reduce the desired effect without substantial cytotoxic effect on non-tumor cells. However, the therapeutically effective amount of the photoactivatable lipid-based nanoparticle or composition will be dependent on the subject being treated, the size and characteristics of the tumor, and the manner of administration of the therapeutic composition.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

Z-average size: An average size determined by analyzing dynamic light scattering data using the technique of cumulants; also referred to as the 'cumulants mean' or the 'harmonic intensity averaged particle diameter' (ISO 22412).

II. Photoactivatable Lipid-Based Nanoparticles

Embodiments of photoactivatable lipid-based nanoparticles (liposomes) include a vesicle wall surrounding a cavity. The vesicle wall comprises a lipid bilayer comprising molecules of at least two liposome-forming lipids and a photosensitizing agent within the lipid bilayer. The lipid bilayer that forms the vesicle wall has an external surface (the exterior of the liposome) and an internal surface that forms the external limit on the enclosed cavity. The photosensitizing agent is a near-infrared wavelength-specific photoreactive agent, primarily lipidic or hydrophobic in nature. The liposome may further include at least one agent within the cavity. Embodiments of the disclosed liposomes have a diameter ranging from 80 nm to 200 nm, such as from 80 nm to 125 nm.

The lipid bilayer includes a non-saturated lipid and a non-polymerizable, saturated lipid, wherein the saturated lipid is the matrix (or bulk) lipid. The photosensitizing agent is located within the lipid bilayer. For in vivo applications, the lipid bilayer may further include a stabilizing lipid to increase blood circulation time. Each of the lipids may be phospholipids.

In some embodiments, the lipid bilayer includes 1,2-bis(tricosa-10,12-diynoyl)-sn-glycero-3-phosphocholine ($DC_{8,9}PC$) as the non-saturated lipid and a tetrapyrrollic photosensitizer, such as 2-[1-hexyloxyethyl]-2-devinyl pyropheophorbide-a (HPPH) as the photosensitizing agent. The saturated lipid is selected based at least in part on the lipid bilayer structure formed when the $DC_{8,9}PC$ and saturated lipid are combined to form the lipid bilayer. Desirably, as the lipid bilayer forms, it will include segregated regions ("pockets") of $DC_{8,9}PC$ and regions of the saturated lipid instead of a more homogeneous combination of the lipids. An exemplary lipid suitable for forming this pocket morphology is dipalmitoylphosphatidylcholine (DPPC). Tetrapyrrolic photosensitizer analogs that may also be useful include those disclosed, for example, in WO 2012/006009.

For in vivo applications, the vesicle wall further includes a stabilizing lipid, such as a PEGylated lipid that reduces uptake of the liposome by the reticuloendothelial system and increases blood circulation time of the liposome. In some embodiments, the PEGylated lipid is 1,2-distearoyl-sn-glycero-3-phosphoethanolamine-N-methoxy(polyethylene glycol) (DSPE-PEG). In some examples, the PEG portion of the DSPE-PEG has a molecular weight of approximately 2,000 daltons, i.e., DSPE-PEG2000. An exterior surface including PEG increases in vivo stability and blood circulation time of liposomes by protecting liposomes from detection by the reticuloendothelial system. FIG. 1 includes the chemical structures of the foregoing compounds.

The lipid bilayer may include from 10 mol % to 50 mol % $DC_{8,9}PC$. In some embodiments, the lipid bilayer includes from 10 mol % to 20 mol % $DC_{8,9}PC$ since $DC_{8,9}PC$ concentrations greater than 20 mol % may decrease stability of the lipid bilayer. The lipid bilayer further may include from 3 mol % to 5 mol % DSPE-PEG. In some embodiments, the lipid bilayer comprises 4 mol % DSPE-PEG2000. In certain examples, the lipid bilayer includes 76-86 mol % DPPC, 10-20 mol % $DC_{8,9}PC$, and 4 mol % DSPE-PEG2000.

HPPH, a photosensitizing agent, is distributed within the lipid bilayer. HPPH is a lipophilic compound with a log P of 5.6 at physiological pH. HPPH has a large molar extinction in the near-infrared region, i.e., $\varepsilon=47,500$ $M^{-1}$ $cm^{-1}$ at 665 nm. HPPH has a singlet oxygen yield of 0.48. HPPH also has anti-cancer properties, and has been used in photodynamic therapy (PDT), e.g., for treatment of esophageal cancer and non-small cell lung cancer. HPPH is in clinical trials as a promising PDT drug. In some embodiments, liposomes are prepared with HPPH at a lipid:HPPH weight ratio ranging from 80:1 to 10:1, such as from 40:1 to 10:1, or from 20:1 to 10:1. In some embodiments, more than 80% of the added HPPH is incorporated into the lipid bilayer. In certain examples, the liposome includes a lipid:HPPH weight ratio from 80:1 to 10:1, such as from 20:1 to 10:1. Without wishing to be bound by a particular theory of operation, HPPH preferentially intercalates into $DC_{8,9}PC$ regions, or pockets, within the lipid bilayer due to its hydrophobic structure. This segregation of HPPH into $DC_{8,9}PC$ pockets is believed to promote lipid bilayer destabilization by inducing a change in the characteristics of the lipid bilayer upon photoactivation of HPPH with light of sufficient intensity and wavelength.

In some embodiments, the lipid bilayer consists essentially of DPPC, $DC_{8,9}PC$, DSPE-PEG2000, and HPPH. For example, the lipid bilayer may have a lipid composition consisting essentially of 76-86 mol % DPPC, 10-20 mol % $DC_{8,9}PC$, and 4 mol % DSPE-PEG2000, and have a lipid:HPPH weight ratio from 80:1 to 10:1.

In some embodiments, the photoactivatable lipid-based nanoparticle further includes a pharmaceutical agent within the cavity defined by the lipid bilayer. Advantageously, the presence of HPPH during liposome formation enhances entrapment of at least some pharmaceutical agents in the liposome cavity. $DC_{8,9}PC$ also increases entrapment of at least some solutes. The pharmaceutical agent may be, for example, a bioactive agent, an imaging agent, or an siRNA molecule. In certain embodiments, the bioactive agent is an anti-cancer agent, such as an anti-tumor agent or an angiogenesis inhibitor. Anti-cancer agents are described for example in Slapak and Kufe, Principles of Cancer Therapy, Chapter 86 in *Harrison's Principles of Internal Medicine,* 14th edition; Perry et al., Chemotherapy, Ch. 17 in Abeloff, *Clinical Oncology* 2nd ed., 2000 Churchill Livingstone, Inc; Baltzer and Berkery. (eds): *Oncology Pocket Guide to Chemotherapy,* 2nd ed. St. Louis, Mosby-Year Book, 1995; Fischer Knobf, and Durivage (eds): *The Cancer Chemotherapy Handbook,* 4th ed. St. Louis, Mosby-Year Book, 1993. Types of suitable anti-cancer agents may include alkylating agents, anti-metabolites, plant alkaloids and terpenoids (e.g., vinca alkaloids and taxanes), topoisomerase inhibitors, cytotoxic antibiotics, and angiogenesis inhibitors. Exemplary anti-cancer agents include, but are not limited to, 5-fluorouracil (5-FU), azathioprine, cyclophosphamide, cytosine arabinoside, antimetabolites (such as Fludarabine), antineoplastics (such as Etoposide, Doxorubicin, daunorubicin, methotrexate, and Vincristine), rapamycin, carboplatin, cis-platinum, irinotecan, lurtotecan, topotecan, campthecines, and the taxanes, such as taxol (Paclitaxel). Anti-inflammatory agents include, but are not limited to, steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, and tolmetin. Alternatively, the agent may be an imaging agent that identifies targeted tissue (such as a tumor) by concentrating a detectable material in the target tissue. Examples of imaging agents include fluorescent dyes, radioactive labels, metal chelates, and other contrast agents (such as iodinated compounds, $^{99m}Tc$ complexes (ex., $^{99m}Tc$-albumin), $^{186}Re$ complexes, gas bubbles, magnetite) that are detectable by suitable means such as radiography, magnetic resonance imaging, computed tomography, etc. Additional agents that may be incorporated into liposomes include, but are not limited to, nucleic acids (e.g., oligonucleotides (DNA, RNA), antisense oligonucleotides, siRNAs, E1A gene, and plasmids such as HLA-B7), amphotericin B, N-(phosphonoacetyl)-L-aspartate, adriamycin, tretinoin, nystatin, prostaglandin E1, adenosine triphosphate, coenzyme Q10, and benzophorphyrin derivatives.

For certain imaging purposes, e.g., bio-distribution studies, trace amounts of a lipid probe (e.g., 1,1'-dioctadecyltetramethyl indotricarbocyanine iodide (DiR)) may be included in the liposomes.

Figure 2:
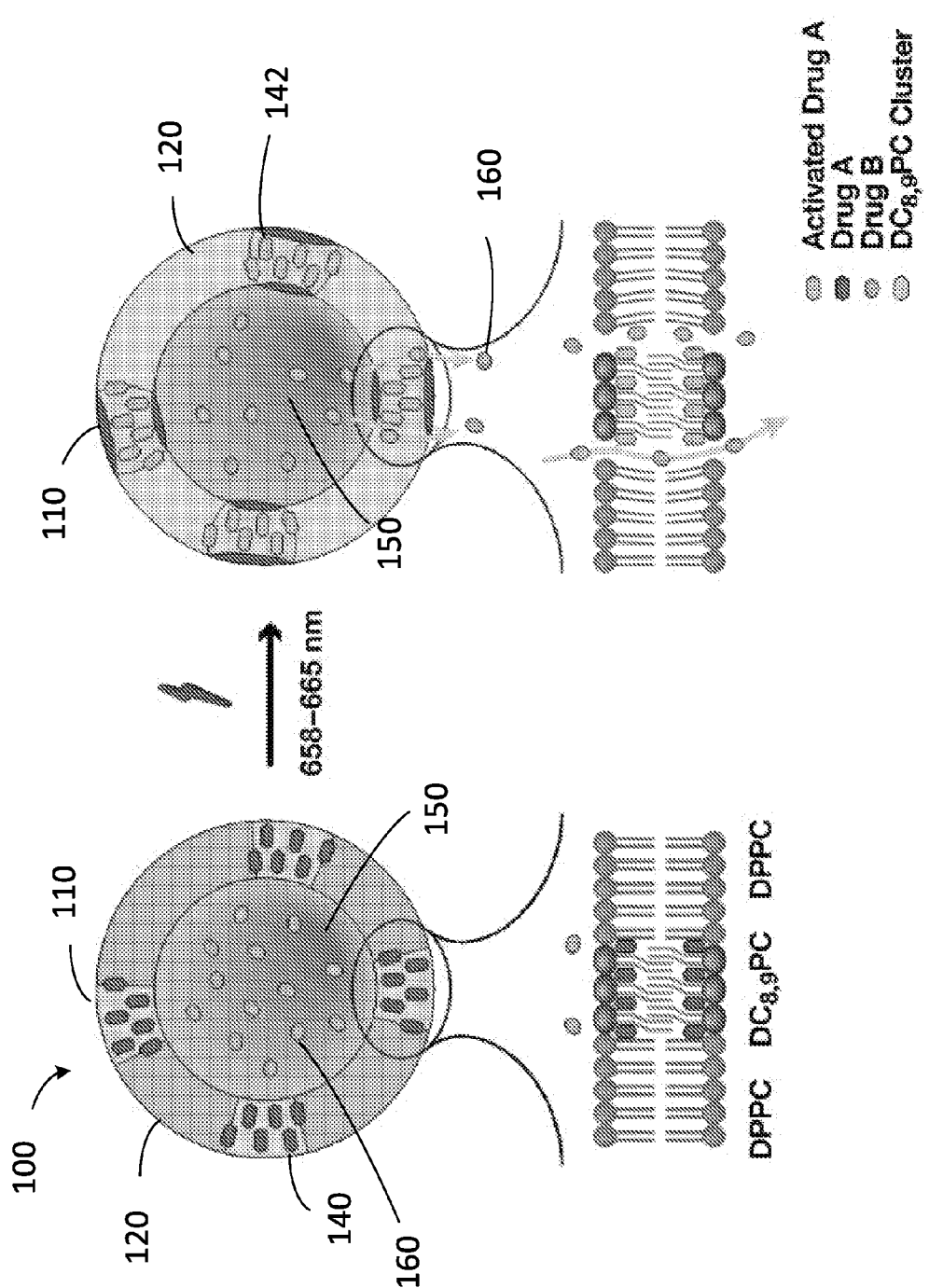
FIG. 2 is a schematic diagram illustrating a photoactivatable lipid-based nanoparticle (liposome) as disclosed herein and disruption of the liposome when irradiated with near-infrared light. The diagram illustrates selective segregation of drug A with $DC_{8,9}PC$ in the liposome's lipid bilayer to form pockets having a modifiable architecture that is changed by exposure to light to disrupt the lipid bilayer, thereby activating Drug A and delivering Drug B from the cavity within the liposome.

FIG. 2 illustrates a liposome 100 as disclosed herein. The liposome 100 includes regions (or "pockets") of $DC_{8,9}PC$ 110, regions of DPPC 120, and HPPH 140 (Drug A), which together form a lipid bilayer that defines a cavity 150. In some embodiments, the liposome further includes DSPE PEG2000 (not shown). An agent 160 (Drug B) is within the cavity 150. As shown in the figure, HPPH 140 preferentially (but not exclusively) segregates into the $DC_{8,9}PC$ pockets 110 for more disruption of the lipid bilayer upon photoactivation of the liposome. When exposed to near-infrared light (e.g., 658-665 nm), activated HPPH 142 (activated Drug A) is formed and destabilization of the lipid bilayer occurs, releasing at least a portion of the agent 160 from the cavity 150 to target tissue.

Activated HPPH is an effective drug for photodynamic therapy. Activated HPPH exerts its therapeutic effect through reactive oxygen species (e.g., singlet oxygen) generated upon photoactivation. Thus, when the liposome includes a drug in the cavity, light activation of HPPH and disruption of the liposome results in dual drug delivery proximal to the liposome site, i.e., activated HPPH and the agent released from the cavity. When the agent is a bioactive agent such as an anti-cancer agent, embodiments of the disclosed liposomes are suitable for delivering combination chemotherapy upon light activation and subsequent liposomal disruption.

Figure 6:
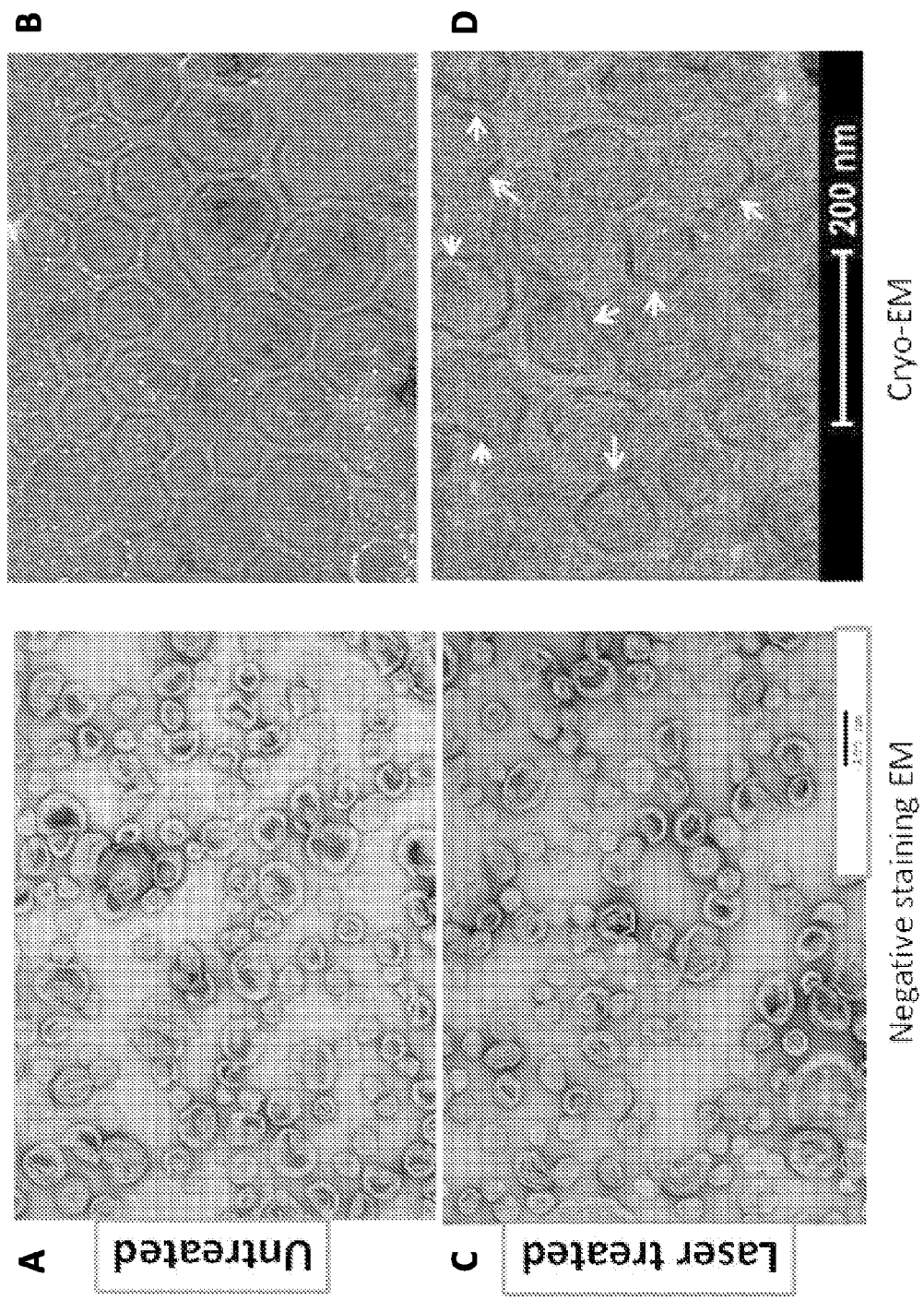
FIG. 6 is a series of photographs obtained by negative-staining electron microscopy (panels A and C) and cryo-electron microscopy (panels B and D) showing untreated and laser treated liposomes including HPPH and calcein; panels A and B are photographs of untreated liposomes; panels C and D are photographs of laser-treated liposomes.

As demonstrated in Example 1, near-infrared light exposure affects morphology of the liposome without disrupting it (see, e.g., FIG. 6). Because the liposomal structure is not destroyed, the agent may be released gradually from the cavity. Thus, in some embodiments, the liposome may act as a "depot," providing potential for repeated light treatments with additional activation of HPPH and/or release of agent.

III. Method of Making Photoactivatable Lipid-Based Nanoparticles

Embodiments of the disclosed photoactivatable lipid-based nanoparticles can be prepared using the techniques described in Yavlovich et al., *J. Therm. Anal. Calorim.* 2009, 98, 97-104. Briefly, lipids (e.g., DPPC and $DC_{8,9}PC$) in chloroform are mixed in the desired ratio, and the chloroform is removed to form a lipid film. The lipid film is then resuspended in a buffer (e.g., HEPES-buffered saline). HPPH and other desired agent(s) are added to the resuspended lipids. The suspension is thoroughly mixed and heated above the phase-transition temperature for the matrix lipid (e.g., DPPC). The phase-transition temperature is the temperature at which a liposome changes from a gel to a liquid-crystalline phase. Lipids are thoroughly dispersed using one or more freeze-thaw cycles. Liposomes are formed by alternating periods of sonication followed by periods of rest. In some examples, 5-10 cycles of sonication and rest were used. Unincorporated molecules are separated from the liposomes by any suitable method, such as size-exclusion gel chromatography.

IV. Pharmaceutical Compositions

This disclosure includes pharmaceutical compositions comprising at least one photoactivatable lipid-based nanoparticle, or liposome, as disclosed herein. Some embodiments of the disclosed pharmaceutical compositions, when irradiated with near-infrared energy, are capable of killing or inhibiting tumor cells, thereby eliminating a tumor, reducing tumor size, and/or inhibiting tumor growth. The pharmaceutical compositions may be applied to tumor cells in vitro, or the pharmaceutical composition may be formulated for use in human and/or veterinary medicine and may be applied to tumor cells in vivo by administering a therapeutically or diagnostically effective amount of the pharmaceutical composition to a subject.

Some embodiments of the pharmaceutical compositions include a pharmaceutically acceptable carrier and at least one active ingredient. Useful pharmaceutically acceptable carriers and excipients are known in the art. Active ingredients may comprise, for example, at least one liposome as described herein, or any combination of liposomes as described herein. In addition, other medicinal or pharmaceutical agents, for example, with similar, related or complementary effects on the affliction being treated, may be included as active ingredients in pharmaceutical compositions. These agents include, but are not limited to, pharmaceutical compounds, chemotherapeutic agents, cytokines, and anti-angiogenic agents.

The pharmaceutical compositions comprising one or more liposomes may be formulated in a variety of ways depending, for example, on the mode of administration and/or on the location and type of disease to be treated. For example, parenteral formulations may comprise injectable fluids that are pharmaceutically and physiologically acceptable fluid vehicles such as water, physiological saline, other balanced salt solutions, aqueous dextrose, glycerol or the like. Excipients may include, for example, nonionic solubilizers, such as cremophor, or proteins, such as human serum albumin or plasma preparations. If desired, the pharmaceutical composition to be administered may also contain non-toxic auxiliary substances, such as wetting or emulsifying agents, preservatives, and pH buffering agents and the like, for example, sodium acetate or sorbitan monolaurate.

The dosage form of the pharmaceutical composition will be determined by the mode of administration chosen. Embodiments of the disclosed pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

Topical preparations may include eye drops, gels, ointments, creams, suspensions, sprays and the like as are well-known in the art.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. The composition may take such forms as suspension, solutions or emulsions in oily or aqueous vehicles, and may contain formulatory agents such as suspending, stabilizing and/or dispersing agents. For example, parenteral administration may be done by bolus injection or continuous infusion. Alternatively, the active ingredient may be in powder form for reconstitution with a suitable vehicle, e.g. sterile water, before use.

Systemic formulations include those designed for administration by injection, e.g., subcutaneous, intravenous, intramuscular, intrathecal or intraperitoneal injection, as well as those designed for transdermal, transmucosal, oral or pulmonary administration.

Oral formulations may be liquid (e.g., syrups, solutions or suspensions), or solid (e.g., powder, tablets, or capsules). Oral formulations may be coupled with targeting ligands for crossing the endothelial bather. Some liposome formulations may be dried, e.g., by spray-drying with a disaccharide, to form liposomal powders. Solid compositions prepared by conventional means with pharmaceutically acceptable excipients such as binding agents (e.g., pregelatinised maize starch, polyvinylpyrrolidone or hydroxypropyl methylcellulose); fillers (e.g., lactose, mannitol, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings that mitigate acid denaturation of the liposome's lipid bilayer. Actual methods of preparing such dosage forms are known, or will be apparent, to those skilled in the art.

Liquid preparations for oral administration may take the form of, for example, elixirs, solutions, syrups or suspensions. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p- hydroxybenzoates or sorbic acid). The preparations may also contain buffer salts, preservatives, flavoring, coloring and sweetening agents as appropriate. Preparations for oral administration may be suitably formulated to give controlled release of the active compound, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases such as cocoa butter or other glycerides.

For nasal administration or administration by inhalation or insufflation, the active compound(s) can be conveniently delivered in the form of an aerosol spray or mist from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount.

For prolonged delivery, the liposomes can be formulated as a depot preparation for administration by implantation or intramuscular injection. Alternatively, transdermal delivery systems manufactured as an adhesive disc or patch which slowly releases the liposome for percutaneous absorption may be used. To this end, permeation enhancers may be used to facilitate transdermal penetration of the active compound (s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Certain embodiments of the pharmaceutical compositions comprising liposomes as described herein may be formulated in unit dosage form suitable for individual administration of precise dosages. The pharmaceutical compositions may, if desired, be presented in a pack or dispenser device which may contain one or more unit dosage forms containing the liposomes. The pack may, for example, comprise metal or plastic foil, such as a blister pack. The pack or dispenser device may be accompanied by instructions for administration. The amount of liposomes administered will depend on the subject being treated, the severity of the affliction (e.g., the size, location, and characteristics of a tumor), and the manner of administration, and is known to those skilled in the art. Within these bounds, the formulation to be administered will contain a quantity of the liposomes disclosed herein in an amount effective to achieve the desired effect in the subject being treated.

Embodiments of the disclosed liposomes will generally be used in an amount effective to achieve the intended result, for example in an amount effective to treat or image a tumor. The liposomes may be administered therapeutically to achieve therapeutic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also includes halting or slowing the progression of the disease, regardless of whether improvement is realized. In some embodiments, the liposomes are administered to achieve diagnostic benefit. Diagnostic benefit includes, for example, the ability to image target tissue such as tumor tissue.

The amount administered will depend upon a variety of factors, including, for example, the particular indication being treated, the mode of administration, the severity of the indication being treated, the age and weight of the patient, the bioavailability of the particular bioactive agent included in the cavity of the liposome, etc. Determination of an effective dosage is well within the capabilities of those skilled in the art.

Effective dosages may be estimated initially from in vitro assays. For example, an initial dosage may be formulated to achieve a tumor tissue concentration of released bioactive agent following liposome disruption that is sufficient to cause tumor cell necrosis as determined in an in vitro assay. Calculating dosages to achieve such concentrations is well within the capabilities of skilled artisans. For guidance, the reader is referred to Fingl & Woodbury, "General Principles," In: Goodman and Gilman's The Pharmaceutical Basis of Therapeutics, Chapter 1, pp. 1 46, latest edition, Pagamonon Press, and the references cited therein.

Initial dosages can also be estimated from in vivo data, such as animal models. Animal models useful for testing the efficacy of compounds to treat tumors are well-known in the art. Ordinarily skilled artisans can routinely adapt such information to determine dosages suitable for human administration.

Preferably, the liposomes will provide therapeutic or prophylactic benefit without causing substantial toxicity. Toxicity of the liposomes may be determined using standard pharmaceutical procedures. The dose ratio between toxic and therapeutic effect is the therapeutic index. Liposomes that exhibit high therapeutic indices are preferred.

Certain embodiments of the pharmaceutical methods and compositions include co-administration of the liposome as described herein and a therapeutically effective amount of a second agent other than the liposome. The liposome and the second agent may be administered either separately or together in a single composition. The second agent may be, for example, an anti-tumor agent or an angiogenesis inhibitor.

V. Photoactivation

Embodiments of the disclosed lipid-based nanoparticles are photoactivated by targeted application of light having a desired wavelength, intensity, and/or surface area to a preselected target area for an effective period of time. The wavelength is selected within the near-infrared range, e.g., from 650 nm to 2500 nm. When HPPH is used as a photosensitizer, the wavelength is selected from 650-670 nm. Suitable light intensities may range from 1 mW to 500 mW depending on the target site and method of application. In some examples, a 90 mW, 660 nm laser was used. Near-infrared light sources can be obtained from commercial sources, including Thorlabs (Newton, N.J.), Laser Components, USA (Hudson, N.H.), ProPhotonix (Salem, N.H.) and others.

In some embodiments, photoactivation is performed by external application of light to a targeted area. NIR light is capable of penetrating transcutaneously into tissue to a depth of several centimeters. In other embodiments, photoactivation may be performed by internal application of light, such as by using an endoscope or a fiber optic catheter. Internal application may be used when the target tissue, such as a tumor, is located at a depth that is unsuitable for external light application. For example, an endoscope may be used for light delivery into the lungs, stomach, or bladder.

The surface area for light application is generally selected to include the target tissue, e.g., a tumor or portion of a tumor, or an area of skin external to the target tissue. When targeted application of external light is desired, the surface area can be controlled by use of an appropriate light applicator, such as a micro-lens, a Fresnel lens, or a diffuser arrangement. For targeted internal light application, a desired endoscope or fiber optic catheter diameter can be selected. In some applications, an indwelling catheter filled with a light scattering solution may be internally placed proximate the target tissue, and an optical fiber light source may be inserted into the catheter (see, e.g., Madsen et al., *Lasers in Surgery and Medicine* 2001, 29, 406-412).

Photoactivation is performed for a period of time effective to activate at least a portion of the HPPH within the liposome's lipid bilayer wall, thereby destabilizing the lipid bilayer wall and releasing at least a portion of an agent with the liposomal cavity. In some embodiments, the effective period of time ranges from several seconds to several minutes, e.g., from 30 seconds to 15 minutes. In certain examples, photoactivation was performed for 5-10 minutes.

VI. Methods of Using Agent-Loaded, Lipid-Based Nanoparticles

Embodiments of the disclosed agent-loaded, lipid-based nanoparticles are suitable for in vivo administration to a subject. Upon irradiation with near-infrared light energy for an effective period of time, at least a portion of the HPPH is activated and the liposomes release at least a portion of an agent, such as a drug, contained within the cavity defined by the lipid bilayer.

HPPH is activated with near-infrared light energy, such as NIR light having a wavelength of 650 to 680 nm. For example, HPPH can be activated when irradiated for an effective period of time by a laser that produces light having a wavelength of 655-675 nm, e.g., a 660-nm laser. In certain embodiments, HPPH is activated when irradiated with a continuous wave (cw)-diode 600 nm laser source (90 mV) for several seconds to several minutes. Without wishing to be bound by a particular theory of operation, the activated HPPH causes a conformational change in $DC_{8,9}PC$, leading to disruption of the lipid bilayer. A lipid bilayer having a lipid:HPPH weight ratio from 80:1 to 10:0.8 and including 10 mol % to 30 mol % $DC_{8,9}PC$ can be disrupted when irradiated with NIR light for an effective period of time, such as at least 30 seconds. In some embodiments, the effective period of time is from 1-10 minutes. When the lipid bilayer is disrupted, at least a portion of the bioactive agent within the cavity may be released. In some embodiments, at least 10%, at least 20%, at least 40%, or at least 60% of the bioactive agent is released.

Figure 3:
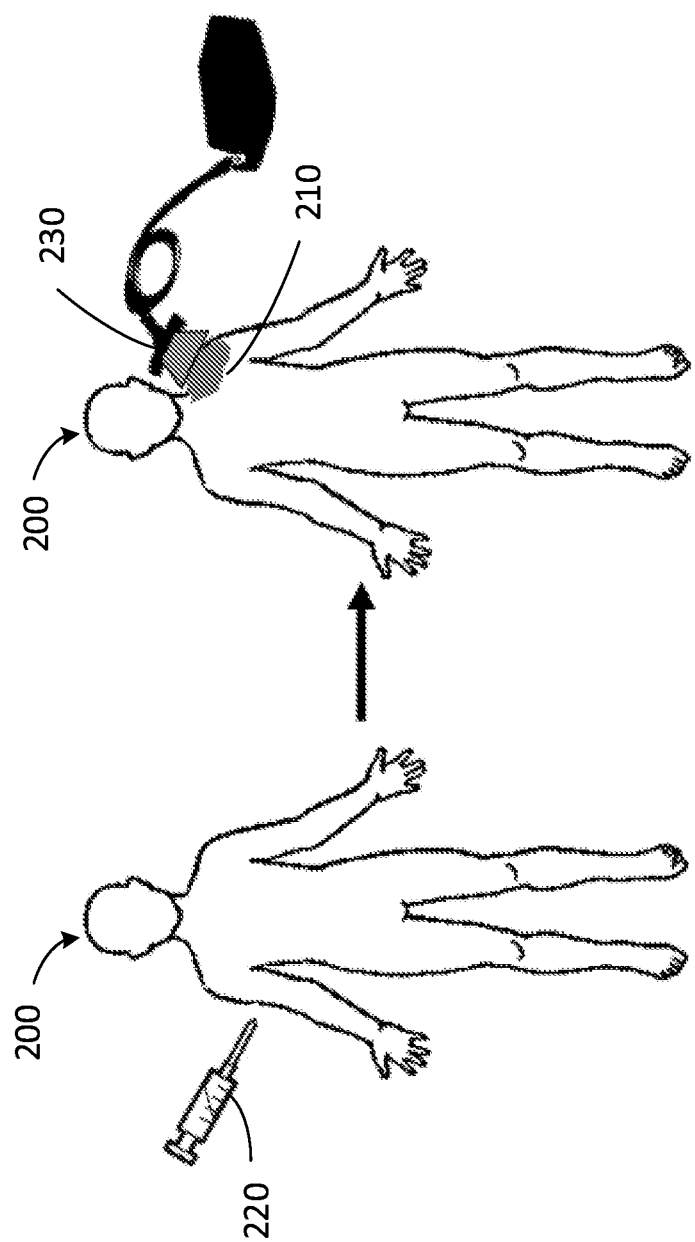
FIG. 3 is a schematic diagram illustrating one embodiment of a method for using the disclosed liposomes to treat a subject having a tumor by injection of the liposomes followed by targeted delivery of light of a desired wavelength to the external surface of the skin.

Embodiments of the disclosed photoactivatable liposomes may be administered to a subject identified as having a condition that may be treated with HPPH, the bioactive agent, or both HPPH and the bioactive agent. For example, with reference to FIG. 3, a subject 200 with a tumor may be treated with liposomes having an anti-tumor agent in the cavity. Administration of the disclosed liposomes to the subject may impair growth of the tumor and/or cause tumor regression. Because tumors typically have "leaky" vasculature, the liposomes preferentially are taken up by and accumulate in the tumor 210. A therapeutically effective amount of the liposomes, or a pharmaceutical composition comprising the liposomes, is administered to the subject by any suitable means including, but not limited to, parenteral, intravenous, subcutaneous, oral, rectal, vaginal, or topical administration. In the example shown in FIG. 3, the liposomes 220 are administered via intravenous injection. A target portion of the subject subsequently is selectively irradiated with NIR light energy of a desired wavelength using an external light applicator 230 for an effective period of time, such as from 1-15 minutes. The light applicator 230 applies the photoactivation energy to a target area limited to the region of the tumor 210, thereby selectively photo activating the liposomes in and around the tumor 210 and targeting delivery of the activated HPPH and/or the anti-tumor agent released from the liposomal cavity. In some examples, tumors were treated in vivo for 5-8 minutes with a continuous wave-diode laser emitting 90 mW at a wavelength of 660 nm.

Both the photoactivated HPPH and the anti-tumor agent may inhibit tumor cell growth and/or kill tumor cells, thereby providing combination chemotherapy to the tumor site. Suitable tumor sites include, but are not limited to, the head, neck, skin, bladder, prostate, colon, and lung. The released bioactive agent is taken up by tumor cells via passive diffusion. Because the drug is released directly at the tumor site, its effectiveness may be increased and/or its side effects may be reduced compared to other methods of non-targeted administration.

Liposomes without an active agent in the cavity also may be effective for treatment of at least some tumors. In an in vitro study, a significant decrease in cell viability was observed when MDA-231 cells/liposome suspensions were treated for 0-5 minutes with a 660 nm laser.

The MDA-MB-231 (containing the luciferase gene) breast cancer mouse model with tumors in both flanks was used for animal studies. Liposomes were injected intravenously, and laser treatments were performed 4 hours post injection. The animals were followed for 15 days post injection. When the liposomes included calcein (a fluorescent marker used as a model active agent) in the cavity, calcein release occurred as indicated by increased fluorescence in the laser-treated portion of the tumor. A concurrent loss of luciferase activity also was observed. A significant decrease in luciferase expression and reduction in tumor volume was observed only in laser-treated animal groups injected with an embodiment of the disclosed liposomes including HPPH (see, e.g., Example 5). Tumor histopathology confirms tumor regression with an indication of tumor necrosis. There was no tumor volume reduction or luciferase expression reduction in tumors that were not laser treated or in animals that received liposomes without HPPH under identical conditions.

Embodiments of the disclosed liposomes, with selection of an appropriate agent for inclusion in the cavity, also may be useful as nano-imaging tools, pathogen diagnostics, oral vaccines, and biomimetics.

VII. Examples

Materials and Methods:

Phospholipids were purchased from Avanti Polar Lipids, Inc. (Alabaster, Ala., USA). Calcein was purchased from Fluka-Sigma-Aldrich (St. Louis, Mo., USA). Sepharose CL-6B was purchased from GE Healthcare (Pittsburgh, Pa., USA). All materials and buffers were reagent grade. 2-[1-hexyloxyethyl]-2-devinyl pyropheophorbide-a (HPPH) was a kind gift from Dr. Thomas Dougherty through material transfer agreement between Roswell park memorial institute, and the National Cancer Institute.

The following general procedures were used, unless otherwise indicated in specific examples.

Liposome Preparation

The following lipids were used at various ratios and/or combinations to prepare liposomes: 1,2-dipalmitoyl-sn-glycero-3-phosphocholine (DPPC), 1,2 bis(tricosa-10,12-diynoyl)-sn-glycero-3-phosphocholine ($DC_{8,9}PC$), 1,2-dioleoyl-sn-glycero-3-phosphocholine (or dioleoyl phosphatidylcholine) (DOPC), 1-palmitoyl-2-oleoyl-sn-glycero-3-phosphocholine (POPC), and 1,2-distearoyl-sn-glycero-3 phosphoethanolamine-N-[methoxy(polyethylene glycol)-2000] (ammonium salt) (DSPE-PEG2000). Several liposome formulations used in this study are shown in Table 1. Liposomes were prepared essentially as described (Yavlovich et al., *J. Therm. Anal. Calorim.* 2009, 98, 97-104). Lipids (in chloroform) were mixed in glass tubes and the solvent was removed under nitrogen gas. The lipid films were kept overnight in a desiccator to remove traces of chloroform. Dried films were then resuspended using HBS (HEPES-buffered saline (10 mM HEPES, 140 mM NaCl), pH=7.4) containing the desired molecules as follows: Typically, the liposomes were prepared from 20 mg total lipid per sample. For calcein-only liposomes, 1 mL 50 mM HBS was added to the lipid films (formulations, II, III &VI). For calcein-HPPH liposomes, 50 mM calcein and 0-2 mg HPPH (from a 100 mg/mL solution in DMSO) were added to the lipid film (formulations, I, IV, and V). Liposomes used in animal and cell viability studies were prepared with an initial lipid:HPPH weight ratio of 10:1. The lipid mixture was vortexed and heated at 51° C. for 20 minutes, above phase-transition temperature for the DPPC matrix lipid. Freeze-thaw cycles were employed to ensure thorough dispersion of lipids throughout the mixture. Probe sonication was used to form the vesicles. The lipid dispersion was sonicated for 1 minute followed by 1 minute of rest. Total sonication was comprised of 5-10 cycles. The lipid dispersion was cooled at 4° C. during the process. Unentrapped molecules were separated from liposomes through size-exclusion gel chromatography using the Sepharose CL-6B column (40×1 cm, 40 mL bed volume). Size analysis was performed to ensure proper liposome size and continuity. Liposomes were passed through a 0.45 μm filter and fluorescence was checked at Ex/Em 490/517 nm, 410/670 nm, and 400/660 for release of calcein, HPPH, and chlorin e6 (respectively) using a fluorescent micro plate reader (SpectraMax M2, Molecular Devices, Sunnyvale Calif., USA). Fluorescence was measured with a fluorescent micro-plate reader before and after addition of Triton™ X-100 (TX-100, 0.02% final concentration) to determine encapsulation efficiency. Total lipid in the samples as determined by phosphorus analysis (Ames et al., *J. Biol. Chem.* 1960, 235, 769-775). For animal studies, 0.5 mol % DiR (Ex/Em 745/840 nm) was included in the lipid mixture when the liposomes were formed (Formulations V and VI, Table 1).

Quantitation of Liposomal HPPH

HPPH incorporation in the liposomes was determined by measuring absorbance at 665 nm using the 96-well plates. The samples (50 μL each) in triplicate were aliquoted a 96 well plate and an equal volume of methanol was added. Subsequently, an additional 50 μL of 1% Triton™ X-100 in HBS was added to the wells. The plates were gently mixed and absorbance was read using the microplate reader. The absorption spectra of liposomes that contained only calcein, HPPH or both also were recorded to confirm that there was no contribution of calcein at 665 nm. A standard curve was generated using the free HPPH under identical experimental conditions.

Light Treatment

The liposomes were examined following exposure to or 660 nm laser as follows and 254 nm (UV) treatments were used as controls.

254 nm (UV) treatment: Liposomes (Formulation 1, Table 1) were placed in a 96 well plate and exposed to 254 nm (short-wave UV) light at a distance of 1-2 inches for 0-40 minutes at room temperature. Fluorescence was read before and after treatment at Ex/Em 490/517 nm and 410/670 nm (calcein and HPPH, respectively). Triton™ X-100 was added to samples and the value was taken as 100% release.

660 nm laser treatment: Liposomes (Formulation 1, Table 1) were placed in a microcentrifuge tube and irradiated horizontally with a diode 660 nm laser at room temperature. Irradiation was done for 0-10 minutes, and fluorescence was measured before and after treatment at Ex/Em 490/517 nm and 410/670 nm (calcein and HPPH, respectively). Addition of Triton™ X-100 was used to calculate 100% release of solutes.

Cell Cultures

MDA-MB-231LM$^{Luc+}$ cells, transfected with luciferase, were maintained in DMEM medium (Sigma®), supplemented with 10% FBS (Gibco®) and 1% penicillin and streptomycin (Lonza®) and incubated in 5% $CO_2$ at 37° C. Cells were routinely maintained by passaging when they attained 80% confluency. Prior to injection into the mice, the cells were collected with a sterile plastic scraper, counted and suspended to the desired cell number concentration.

Tumor Growth in Vivo

Mice used in the experiment were 4-5 week old female athymic nude mice from Harlan Sprague Dawley. To induce

TABLE 1

| *Liposome Formulation | Lipid(s) | Ratio DPPC:$DC_{8,9}$PC:DiR | Entrapped Solute | Particle Diameter |
|---|---|---|---|---|
| I | DPPC:$DC_{8,9}$PC | 86:10:0 | Calcein HPPH | 91.2 d · nm ± 0.94 d · nm |
| II | DPPC:$DC_{8,9}$PC | 86:10:0 | Calcein | 88.2 d · nm ± 2.76 d · nm |
| III | DPPC | 96:0:0 | Calcein | 89.0 d · nm ± 0.91 d · nm |
| IV | DPPC | 96:0:0 | Calcein HPPH | 110.9 d · nm ± 0.70 d · nm |
| V | DPPC:$DC_{8,9}$PC:DiR | 86:10:0.5 | Calcein HPPH | 82.5 d · nm ± 0.32 d · nm |
| VI | DPPC:$DC_{8,9}$PC:DiR | 86:10:0.5 | Calcein | |

*All formulations contained 4 mol % DSPE-PEG2000

Liposome Size Analysis

Size and population distribution of liposomes were determined by dynamic light scattering (DLS) measurements using a Malvern instrument (NANO ZS, Malvern Instruments, CA, USA). For a typical sizing experiment 10 μL of liposome solution in 400 μL HBS buffer were placed into a 1.5 mL microcuvette. Each run consisted of 3 measurements of 12 to 20 acquisitions per sample.

tumor growth 1×10$^7$ cells in a total volume of 200 μL were injected subcutaneously in the fat pack of the ribcage on both sides (the positive and the negative group) or on one side (bio distribution group). Tumor growth was monitored every two days by measurement with a digital caliper, and the tumor volume was calculated with the formula: tumor volume=½ (length×width$^2$).

Treatment of Tumors with Laser in Vivo

When the tumors reached a volume of 200-300 mm³, 200 μL of either HPPH-calcein-DiR liposomes (Formulation V, Table 1) or calcein-DiR liposomes (Formulation VI, Table 1) were injected into the tail vein. Four hours after injection, the mice were anesthetized with isoflurane and one tumor per mouse was treated for eight minutes with a continuous wave (cw)-diode laser (Thorlabs, TCLDM9) emitting 90 mW (spot size 0.9 cm Ø) at a wavelength of 658 nm. The second tumor was left untreated as a reference. The mice of the bio-distribution group were left untreated.

Bioluminescence and Fluorescence Imaging

Anesthetized mice were imaged with a custom-built system outfitted with an intensified cooled CCD camera (Princeton Instruments, PIMAX2) nine minutes after an intraperitoneal injection of D-luciferin (10 μL/g body weight of a 15 mg/mL solution, Biotium®). Fluorescence images were taken with the same system but with different excitation and emission filters.

Mice were imaged prior to and after the treatment. Bioluminescence images were also taken 4, 7 and 14 days after treatment. For bio distribution, the mice were imaged prior to injection and at 30 min, 2 hrs, 4 hrs, 6 hrs, 8 hrs, 24 hrs, 48 hrs and 72 hrs after injection.

Tumor Histopathology

Xenografts were fixed in 10% neutral buffered formalin, routinely processed, paraffin-embedded, and sectioned at 5 μm, and stained with hematoxylin and eosin (H&E). Stained sections were scanned into digital format via an Apero Scanscope. All evaluations were performed by a board-certified veterinary pathologist.

Example 1

Encapsulation of HPPH in Liposomes

The basic design of liposomes and projected photo-triggering effects are shown in FIG. 2. The formulations used in this study are shown in Table 1. HPPH incorporation into liposomes that were prepared using DPPC:$DC_{8,9}$PC:DSPE-2000 (86:10:04 mole ratio) was evaluated. Liposomes prepared from DPPC:DSPE-PEG2000 (96:04 mole ratio) and liposomes loaded with calcein only were used as controls (Table 1). For animal studies, trace amounts of a near-IR lipid probe DiR were incorporated, as fluorescence properties of DiR are distinct from HPPH.

Figure 4B:
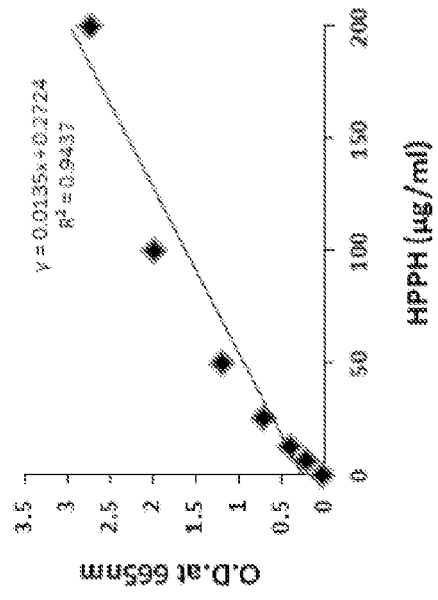
FIG. 4B is a standard curve of absorbance versus concentration for HPPH.
Figure 4A:
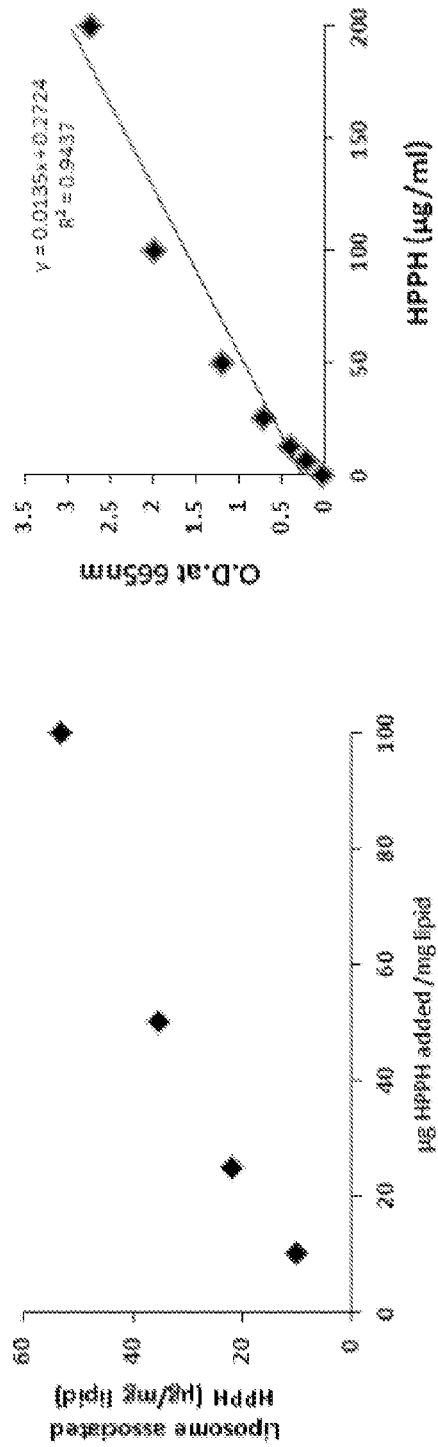
FIG. 4A is a graph of liposome-associated HPPH concentration versus concentration of HPPH added to a liposome formulation including DPPC:$DC_{8,9}$PC:DSPE-PEG2000 with a mole ratio of 86:10:4.
Figure 4C:
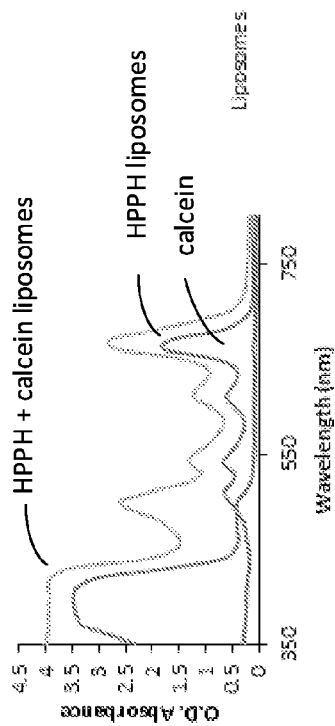
FIG. 4C shows absorbance spectra of liposomes including HPPH, liposomes including calcein, and calcein alone.

Various concentrations of HPPH were added to the known amount of total lipid mixture. Liposomes were prepared in the presence of calcein (Methods section). Liposomes were prepared by hydrating 10 mg lipid films with 1 mL HBS containing 50 mM calcein and various concentrations of HPPH. The lipid:HPPH ratios were 80:1, 40:1, 20:1, and 10:1 on a weight basis. Liposomes were prepared, and any unincorporated HPPH and/or calcein was removed by column chromatography (Methods section). The HPPH was quantitated by measuring absorbance at 665 nm as described in Methods section. The values were normalized to the recovered liposomal lipid content by Pi estimation. A standard curve of free HPPH is shown in FIG. 4B. The ratio of lipid:HPPH up to 10:1 (weight basis) when preparing the liposomes was found to be optimal for maximum HPPH incorporation (FIG. 4A), resulting in a final lipid:HPPH weight ratio of ~0.58 in the prepared liposomes. Since the liposomes also contained calcein, it was confirmed that there was no contribution of calcein at 665 nm in the assay (FIG. 4C).

Figure 5:
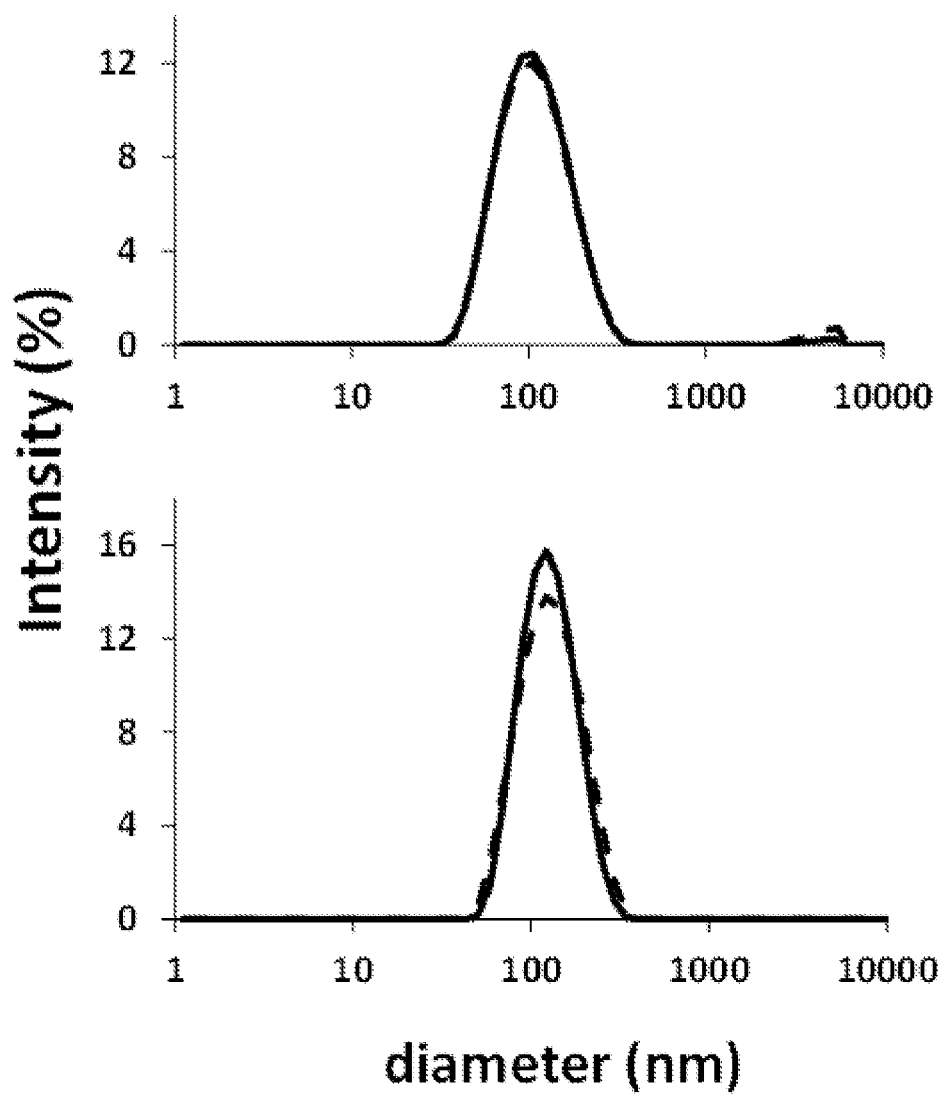
FIG. 5 is a graph comparing the hydrodynamic size of liposomes including HPPH and calcein (upper panel) and liposomes including calcein (lower panel). Untreated samples are shown in broken lines, 5-minute laser-treated samples are shown in solid lines.

Liposome size was determined by dynamic light scattering. As shown in FIG. 5, liposomes including HPPH and calcein (upper panel) had a hydrodynamic size substantially the same as liposomes that included calcein (lower panel). FIG. 5 also shows the effect of 5-minute laser treatment on the size distribution. Broken lines, controls; solid lines, laser-treated samples.

Liposomes including HPPH and calcein further were evaluated by negative-staining electron microscopy and cryo-electron microscopy to determine the morphological changes upon laser treatment (FIG. 6). Panels A and B are negative-staining EM and cryo-EM photographs, respectively, of liposomes prior to laser treatment. Panels C and D are negative-staining EM and cryo-EM photographs, respectively, of liposomes following laser treatment. A comparison of panels A and C shows that the liposome size was relatively unchanged and the laser-treated liposomes remained intact. However, a comparison of panels B and D shows that laser treatment affected the liposomal morphology when HPPH was included. In particular, laser-treated liposomes including HPPH (panel D) showed crenation (as indicated by the arrows), i.e., a scalloped or notched shape, demonstrating that laser treatment restructured morphology of HPPH-containing liposomes.

Example 2

Photo-Triggered Release of Calcein

Calcein release from liposomes containing 12.5-100 μg HPPH/mg lipid (Formulation 1, Table 1) upon treatment with a 660 nm laser was measured as described in the Methods section. Samples were diluted with HBS (1:10 ratio v/v) for laser treatments. 100-150 μL samples were placed in a microcentrifuge tube and irradiated with a 660 nm laser for the indicated times. Calcein fluorescence was measured at 490 nm before and after laser treatment at Ex/Em 490/517 nm. Triton™ X-100 was added for complete release of calcein. Values are expressed as percentage of Triton™ X-100 values as 100%.

Figure 7A:
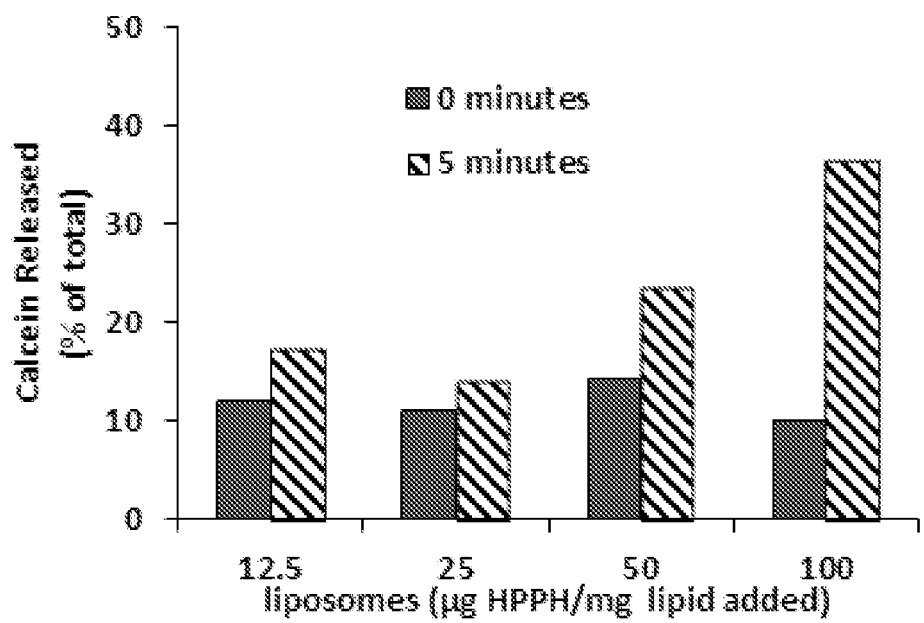
FIG. 7A is a graph showing the percent calcein released as a function of the concentration of HPPH in liposomes including DPPC:$DC_{8,9}$PC:DSPE-PEG2000 with a mole ratio of 86:10:4. The HPPH concentration varied from 12.5-100 μg HPPH/mg lipid. Liposomes were irradiated with a 660 nm laser for 0 minutes and 5 minutes.

Calcein release from all formulations was observed (FIG. 7A). However, liposomes that contained lipid: HPPH at the ratio of 10:1 resulted in significantly higher calcein release. Therefore, this formulation (Table 1, formulation I) was used for further studies. Liposome formulation II (prepared without HPPH) did not release calcein upon 660 nm laser treatment under identical conditions, confirming that HPPH was essential for photo-triggering (data not shown). Calcein release was also observed from liposomes that were prepared with DPPC and HPPH (without $DC_{8,9}$PC, Table 1, formulation IV). However, calcein loading was significantly less (≈40 fold less) and there was spontaneous release of calcein (not shown) in these formulations (Table 2).

Figure 7B:
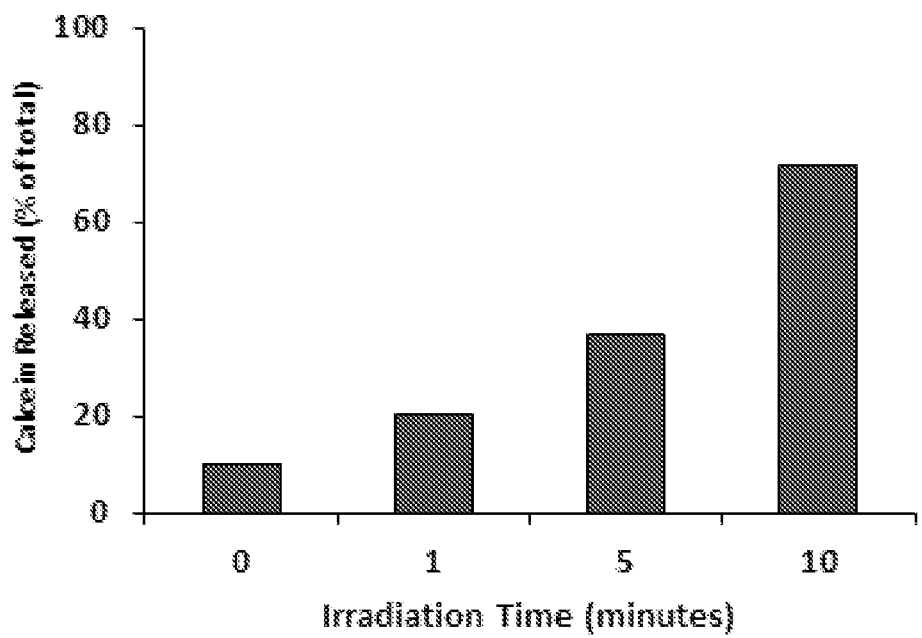
FIG. 7B is a graph showing the percent calcein released as a function of time when irradiated with a 600 nm laser. The liposomes had a lipid:HPPH weight ratio of 10:1 and a DPPC:$DC_{8,9}$PC:DSPE-PEG2000 mole ratio of 86:10:4 (Formulation I).

The effect of irradiation time on calcein release is shown in FIG. 7B. The liposomes had a lipid:HPPH weight ratio of 10:1. Calcein release increased as irradiation time increased with more than 75% calcein release after irradiation for 10 minutes.

TABLE 2

| Formulation | Solute(s) entrapped | Entrapment Efficiency (relative fluorescence units) | |
|---|---|---|---|
| | | Calcein | HPPH |
| DPPC | calcein | $1.1 \times 10^4$ | n/a |
| DPPC:$DC_{8,9}$PC | calcein | $10 \times 10^4$ | n/a |
| DPPC | calcein/HPPH | $4.4 \times 10^4$ | $6.9 \times 10^3$ (±0.15 × 10³) |
| DPPC:$DC_{8,9}$PC | calcein/HPPH | $9.8 \times 10^4$ | $7.9 \times 10^3$ (±0.14 × 10³) |

Example 3

Validation of DPPC:DC$_{8,9}$PC:DSPE-PEG2000 Formulation

The efficacy of DPPC in the liposomal formulations was evaluated. DPPC facilitates formation of DC$_{8,9}$PC pockets, or segregated regions, in the lipid bilayer. Palmitoyl oleoyl phosphatidylcholine (POPC) was evaluated as a potential alternative to DPPC. The liposomes had a ratio of 86 mol % DPPC or POPC, 10 mol % DC$_{8,9}$PC, and 4 mol % DSPE-PEG2000. HPPH was included at an initial lipid:HPPH ratio of 10:1, and calcein was incorporated into the liposomal cavity as described above. The liposome-associated concentrations (expressed per 100 nmol of liposomal lipid) of calcein and HPPH were measured before and after laser-treatment. Concentrations were determined by centrifuging the liposome sample using a 10K molecular weight cut-off filter. The concentrated pellets were resuspended in 300 µL HEPES buffer with saline, pH 7.4-7.5, and transferred to a 96-well plate (100 µL×3). The amounts of HPPH and calcein were determined by absorbance measurement at 665 nm (HPPH) and 490 nm (calcein) using standard curves for HPPH and calcein, respectively. Total lipid content was determined by measurement of inorganic phosphorus. The values are expressed as nmol of calcein or HPPH per nmol lipid in each sample.

Figure 8A:
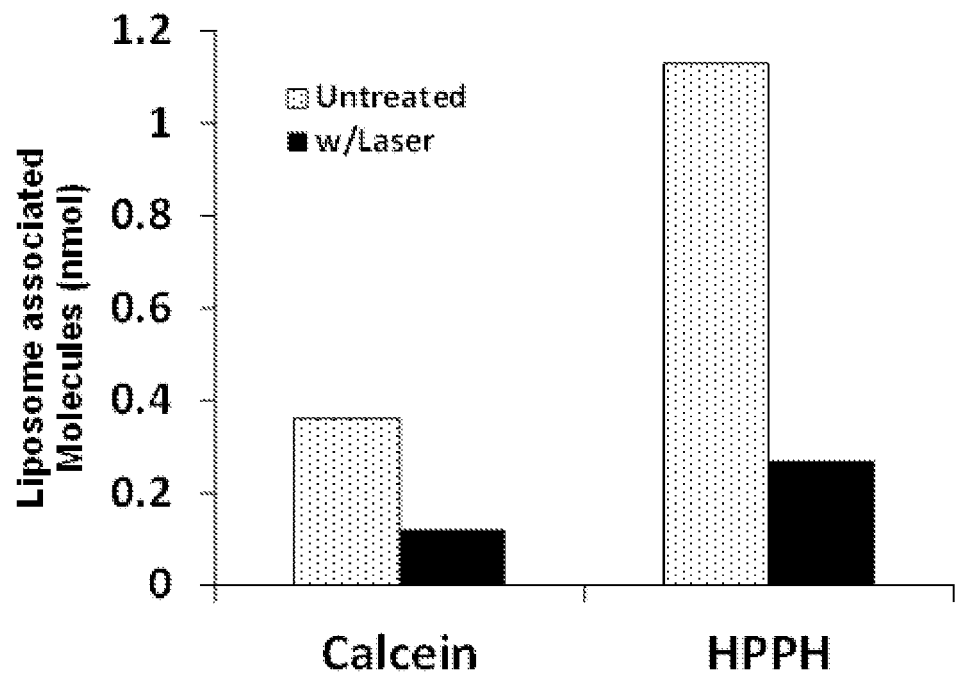
FIG. 8A is a graph showing the liposome-associated concentration of calcein (absorbance at 490 nm) and HPPH (absorbance at 665 nm), before and after laser treatment, in liposomes including DPPC:$DC_{8,9}$PC:DSPE-PEG2000 with a mole ratio of 86:10:4.
Figure 8B:
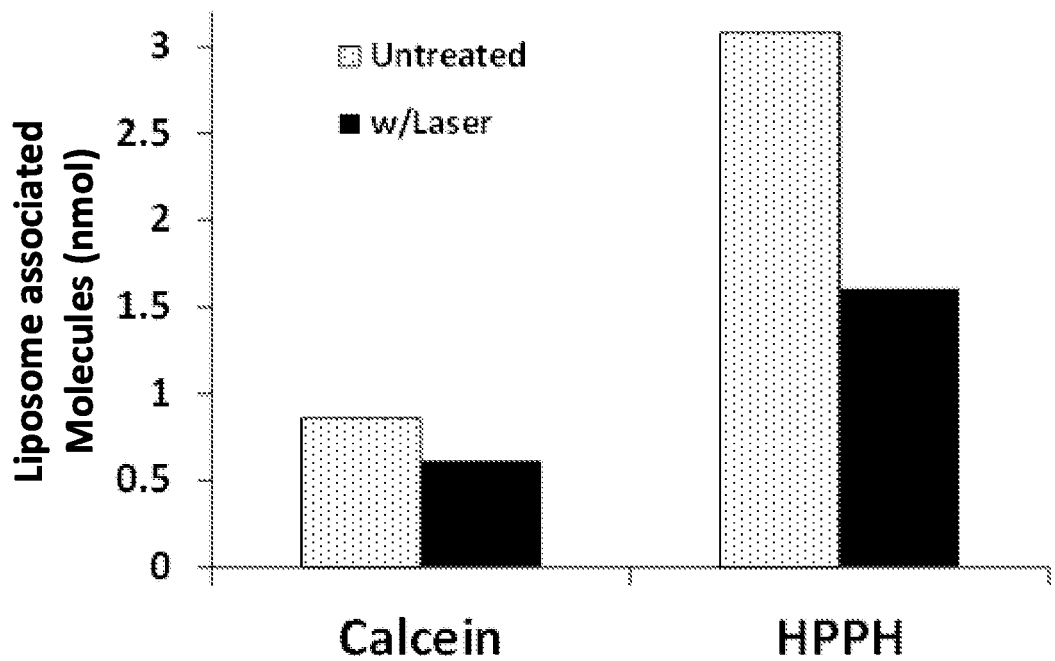
FIG. 8B is a graph showing the liposome-associated concentration of calcein and HPPH, before and after laser treatment, in liposomes including POPC (palmitolyl oleoyl phosphatidylcholine:$DC_{8,9}$PC:DSPE-PEG2000 with a mole ratio of 86:10:4.

When the liposomes were prepared with DPPC, laser treatment resulted in release of more than half of the calcein (FIG. 8A). The HPPH concentration was also diminished by more than 75%, indicating that laser treatment affected the HPPH structure. When the liposomes were prepared with POPC, however, laser treatment resulted in only minimal release of calcein, and a much smaller effect on the HPPH concentration was noted (FIG. 8B). These results demonstrate that DPPC-HPPH formulations are better candidates than POPC-HPPH formulations for photoactivation.

The calcein quenching ratio for each sample was determined by calculating: (1–the ratio of calcein fluorescence before and after treatment with 10 µL of Triton® X-100)× 100. The results are shown in Table 3. A comparison of the HPPH-containing liposomes shows that incorporation of DPPC increases calcein release by a factor of 2 compared to liposomes prepared with POPC.

TABLE 3

| Entrapped Molecule | Matrix Lipid | Change in calcein quenching ratio (%) |
|---|---|---|
| Calcein | DPPC | 1.75 |
| Calcein/HPPH | DPPC | 15.32 |
| Calcein | POPC | 0.50 |
| Calcein/HPPH | POPC | 8.36 |

To further validate the liposome formulation, liposomes comprising dioleoyl phosphatidylcholine (DOPC) were prepared as described in the literature (Noiseux et al., *J. of Biomedical Optics* 2008, 13(4):014313-1 to 041313-11; Mermut et al., *J. of Biomedical Optics* 2008, 13(4):041314-1 to 041314-11). Four liposomal formulations were prepared; calcein was incorporated into the formulations:
 A. DOPC (100 mol %)
 B. DOPC:cholesterol (11.76:4.46 mol ratio)
 C. DOPC:HPPH (11.76:0.1 mole ratio)
 D. DOPC:cholesterol:HPPH (11.76:4.46:0.1 mole ratio)

Figure 9:
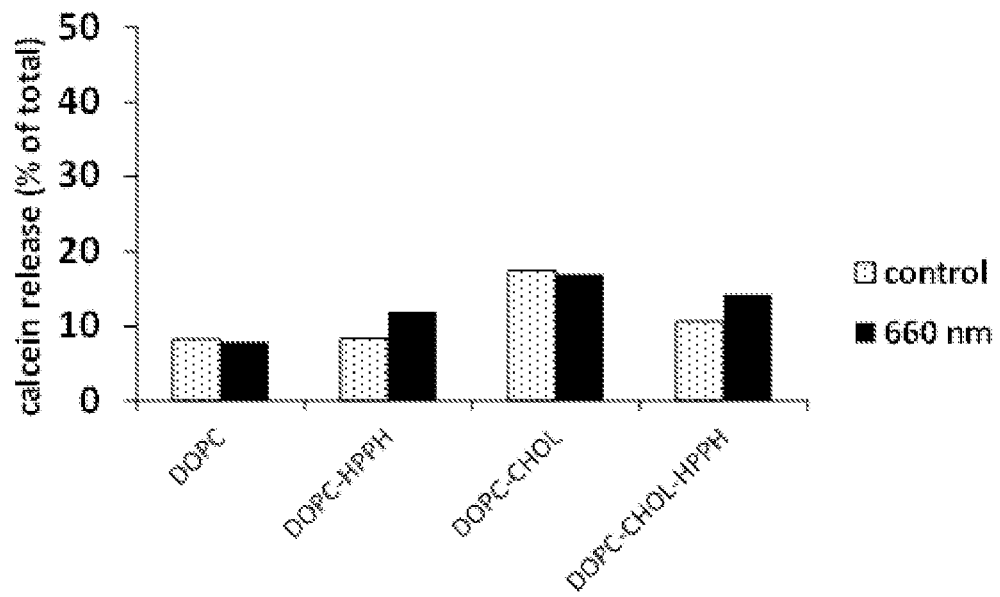
FIG. 9 is a graph illustrating calcein release from liposomes including dioleoyl phosphatidylcholine (DOPC), DOPC-HPPH, DOPC-cholesterol, and DOPC-HPPH-cholesterol.

The release of calcein from each of the formulations was measured before and after laser-treatment. The results are shown in FIG. 9. None of the DOPC-containing formulations released significant amounts of calcein when treated with a 660-nm laser. Thus, HPPH does not promote photoactivation of all liposomes.

Example 4

Validation of HPPH Requirement for Photoactivation

Other photodynamic drugs were evaluated to determine whether they were suitable for producing photoactivatable liposomes. Mitoxantrone and chlorin e6 were evaluated. Mitoxantrone (dihydroxyanthracenedione dihydrochloride) is a type II topoisomerase inhibitor. Chlorin e6 is a member of the chlorin photodynamic therapy drug family.

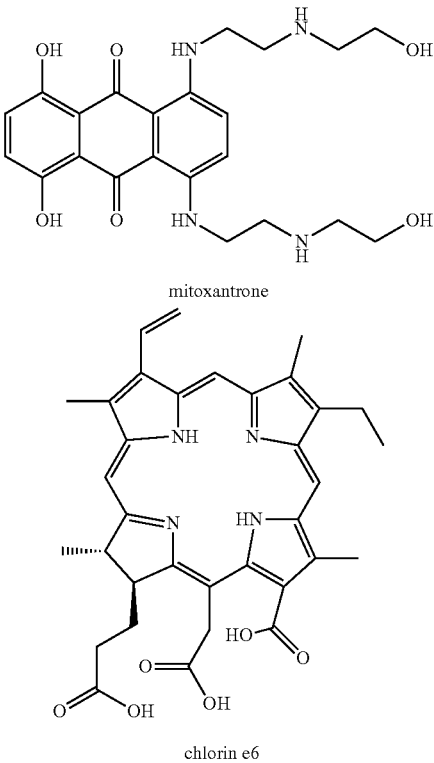

mitoxantrone chlorin e6

Figure 10:
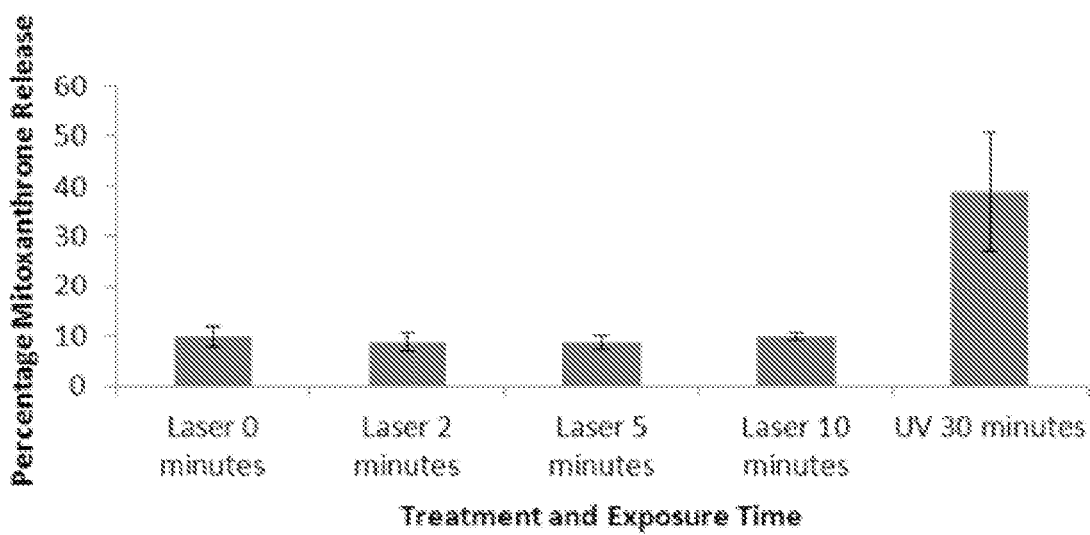
FIG. 10 is a graph illustrating the effect of irradiation for 0-10 minutes with a 660-nm laser on DPPC:$DC_{8,9}$PC:DSPE-PEG2000 liposomes including mitoxantrone.

Mitoxantrone absorbs near-infrared light having wavelengths of 610 and 660 nm. However, DPPC:DC$_{8,9}$PC:DSPE-PEG2000 liposomes including mitoxantrone (8-10 nmol mitoxantrone per 100 nmole lipid) did not release mitoxantrone when irradiated with a 660-nm laser for up to 10 minutes (FIG. 10). As expected, mitoxantrone was released when the liposomes were irradiated with ultraviolet light.

Figure 11A:
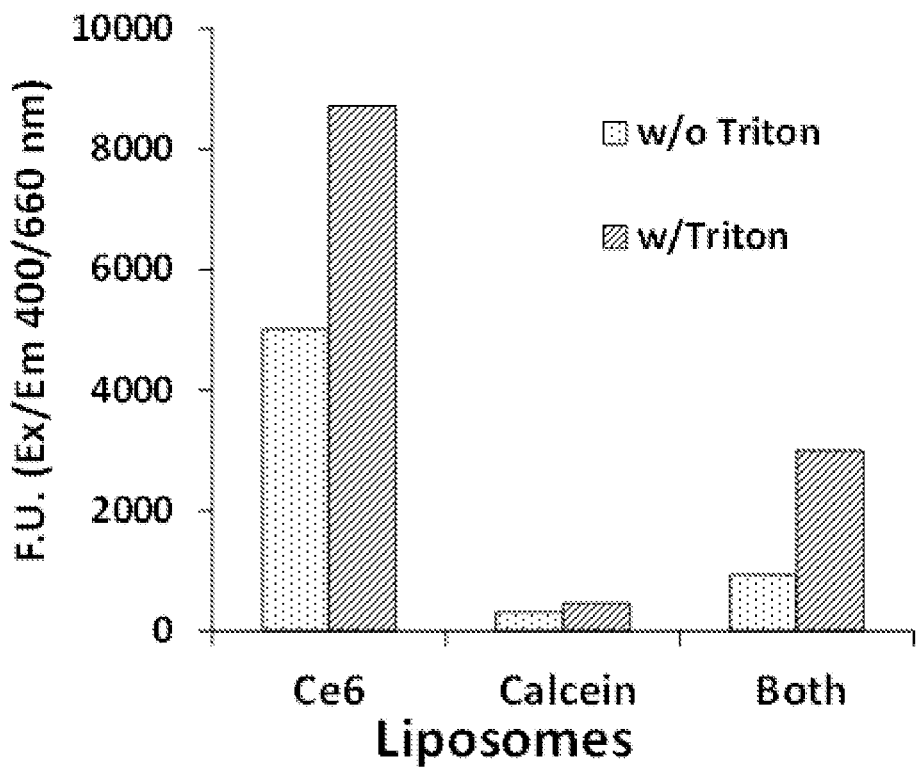
FIG. 11A is a graph illustrating chlorin e6 incorporation into DPPC:$DC_{8,9}$PC:DSPE-PEG2000 in the presence or absence of calcein (Ex/Em=440/660 nm).
Figure 11B:
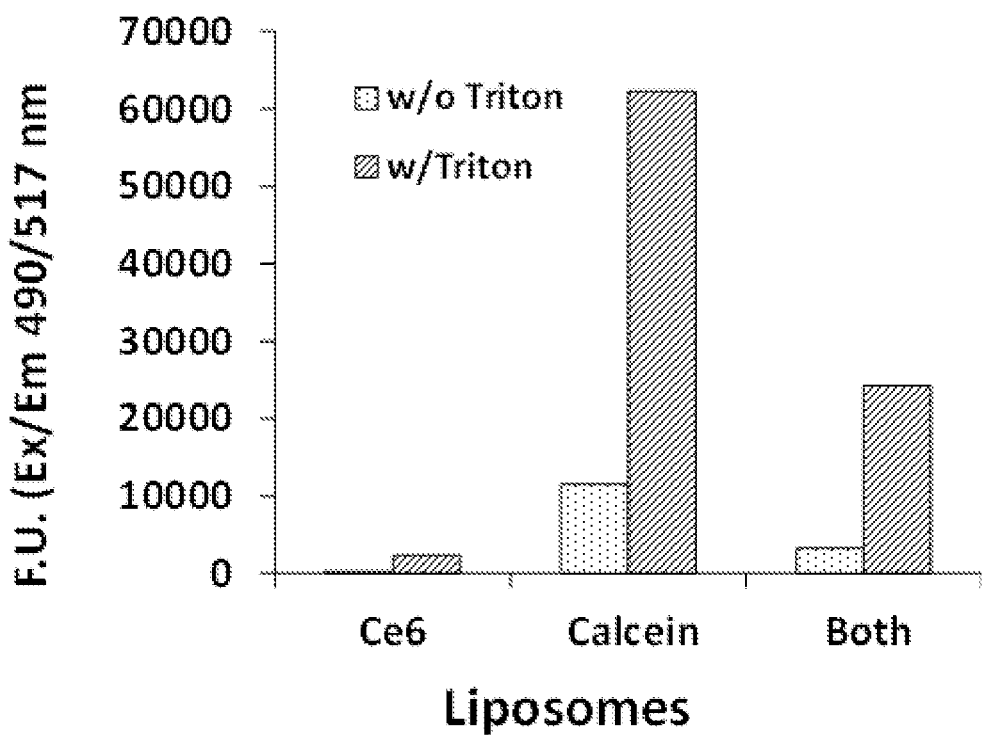
FIG. 11B is a graph illustrating calcein incorporation into DPPC:$DC_{8,9}$PC:DSPE-PEG2000 in the presence or absence of chlorin e6 (Ex/Em=490/517 nm).

Chlorin e6 (Ce6) has a chemical structure very similar to HPPH and absorbs near-infrared light having a wavelength of 650 nm. DPPC:DC$_{8,9}$PC:DSPE-PEG2000 (86:10:4) liposomes were prepared with Ce6, calcein, or Ce6 and calcein. Ce6, when present, was included at an initial lipid:Ce6 weight ratio of 10:1. The liposomes were evaluated for incorporation of Ce6 and calcein. Fluorescence was measured with a fluorescent micro-plate reader before and after addition of Triton™ X-100 to determine encapsulation efficiency. The results are shown in FIGS. 11A and 11B. Although DPPC:DC$_{8,9}$PC:DSPE-PEG2000 liposomes readily incorporated Ce6 (FIG. 11A, "Ce6") or calcein (FIG. 11B, "calcein"), co-encapsulation of Ce6 and calcein resulted in at least a three-fold decrease in loading of both Ce6 (FIG. 11A, "both") and calcein (FIG. 11B, "both"). This observation contrasted with HPPH/calcein liposomes in which co-encapsulation did not negatively affect incorporation of HPPH or calcein.

Figures 12A, 12B, 12C, 12D:
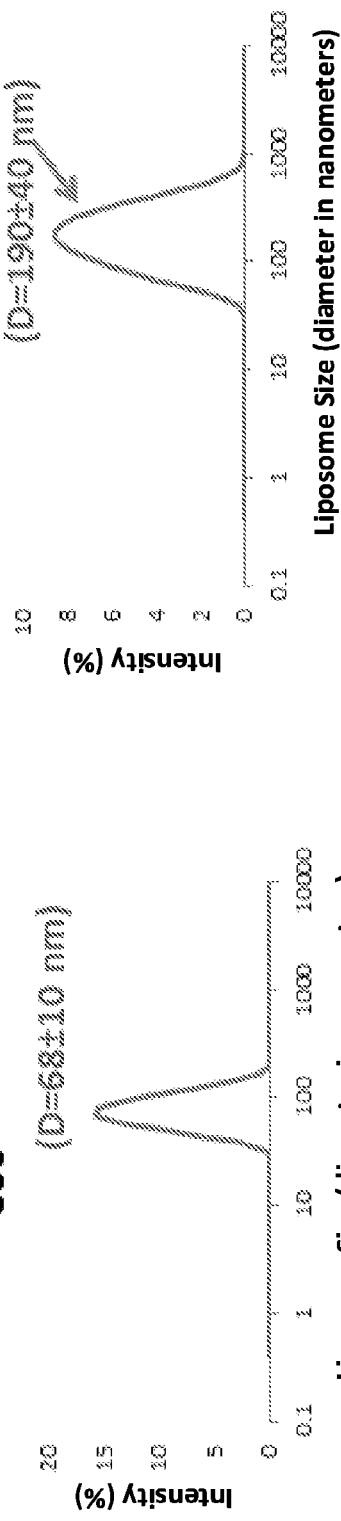
FIGS. 12A-12D are graphs illustrating the sizes of DPPC:$DC_{8,9}$PC:DSPE-PEG2000 liposomes including chlorin e6 (FIG. 12A), calcein (FIG. 12B), chlorin e6 and calcein (FIG. 12C), or HPPH and calcein (FIG. 12D).

Size analysis indicated that liposomes incorporating both Ce6 and calcein were much larger (190±40 nm diameter, FIG. 12C) than liposomes incorporating Ce6 alone (68±10 nm diameter, FIG. 12A), calcein alone (106 nm diameter, FIG. 12B), or HPPH and calcein (91 nm diameter, FIG. 12D). Thus co-encapsulation of Ce6 and calcein produces liposomes that may be unacceptably large for at least some uses.

Figure 13A:
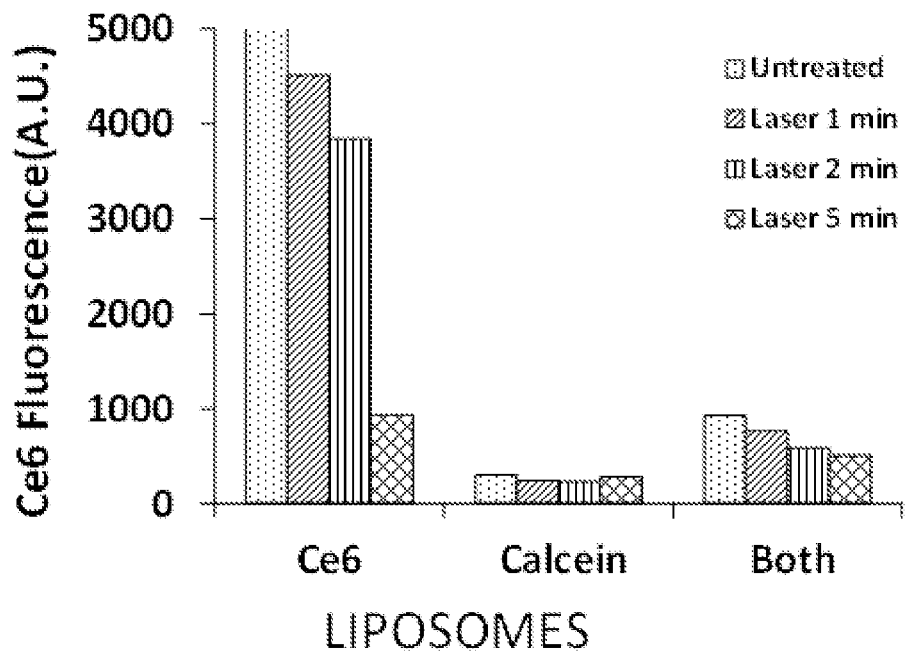
FIG. 13A is a graph illustrating the fluorescence of chlorin e6 in DPPC:$DC_{8,9}$PC:DSPE-PEG2000 liposomes including chlorin e6, calcein, or both after treatment with a 660-nm laser for 1, 2, or 5 minutes (Ex/Em=400/660 nm).
Figure 13B:
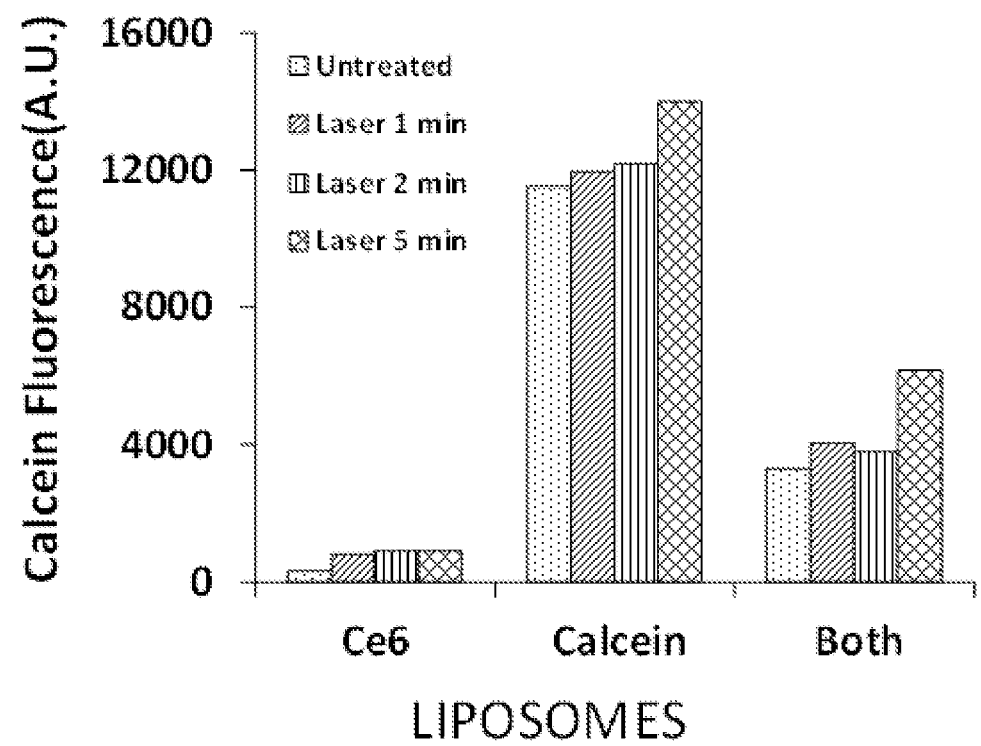
FIG. 13B is a graph illustrating the fluorescence of calcein in DPPC:$DC_{8,9}$PC:DSPE-PEG2000 liposomes including chlorin e6, calcein, or both after treatment with a 660-nm laser for 1, 2, or 5 minutes (Ex/Em=490/517 nm).

The liposomes were irradiated with a 660-nm laser for 1, 2, or 5 minutes, and the fluorescence of Ce6 and calcein was measured. As shown in FIG. 13A, Ce6 was activated as expected by the laser ("Ce6"), and the measured Ce6 concentration decreased over time. The release of calcein was increased slightly after irradiation for 5 minutes when the liposomes included both Ce6 and calcein (FIG. 13B). However, compared to liposomes that included calcein only, the increase was not above background levels.

The foregoing results demonstrated that HPPH was required for effective photoactivation of DPPC:DC$_{8,9}$PC:DSPE-PEG2000 liposomes.

Example 5

Bio-Distribution and Tumor Accumulation of DPPC:DC$_{8,9}$PC Liposomes in Mice

DiR (1,1'-dioctadecyltetramethyl indotricarbocyanine iodide) was used as an imaging probe in animal studies with DPPC:DC$_{8,9}$PC liposomes. Folate was added to some liposome formulations to facilitate tumor targeting in KB xenograft-bearing mice; KB tumors over-express the folate receptor. The following liposomes were prepared: DPPC:DC$_{8,9}$PC:DiR (9:1:0.5 mol %, non-targeted liposomes), DPPC:DC$_{8,9}$PC (9:1 mol %, no DiR for background imaging), and DPPC:DC$_{8,9}$PC:DiR:folate (9:1:0.5:0.5 mol %, targeted liposomes. All liposomes included 4 mol % DSPE-PEG2000.

Imaging studies demonstrated that DiR-containing liposomes, with and without folate, were taken up by normal mice within 0.5 hr. Within 75 hours, the liposomes were concentrated in the animals' livers. Liposomes without DiR were not visualized. After 3 weeks, liposomes were not visible in any of the animals, indicating that liposomes had been cleared from the animals and that the liposomes were not toxic.

DPPC:DC$_{8,9}$PC:DiR:folate (98:10:0.5:0.5 mol %) liposomes were loaded with doxorubicin and injected into mice at a dosage of 0.5 mg or 2.5 mg liposomal lipid. As a control, mice were injected with doxorubicin in the absence of liposomes. Subsequent imaging (Ex=500, Em=600) demonstrated uptake of the liposomes by the liver, kidneys, and spleen, with lesser uptake by the lungs/heart and pancreas. As expected, no fluorescence was observed in the mice that received only doxorubicin.

Liposome uptake in tumor-bearing mice (KB xenografts) was evaluated. Four liposome formulations were prepared:
  A. DPPC:DC$_{8,9}$PC:DiR (89.5:10:0.5 mol %)—Folate$^-$ polymerizable (Z-ave=127.5±1.0 d.nm).
  B. DPPC:DC$_{8,9}$PC:DiR:folate (89:10:0.5:0.5 mol %)—Folate$^+$ polymerizable (Z-ave=89.35±1.0 d.nm).
  C. DPPC:DiR (99.5:0.5 mol %)—Folate$^-$ DPPC (Z-ave=103.9±4.0 d.nm).
  D. DPPC:DiR:folate (99:0.5:0.5 mol %) Folate$^+$ DPPC (Z-ave=144±2.0 d.nm).

All samples included 4 mol % DSPE-PEG2000 and were loaded with doxorubicin. Folate was included in formulations B and D to facilitate tumor targeting.

Figure 14:
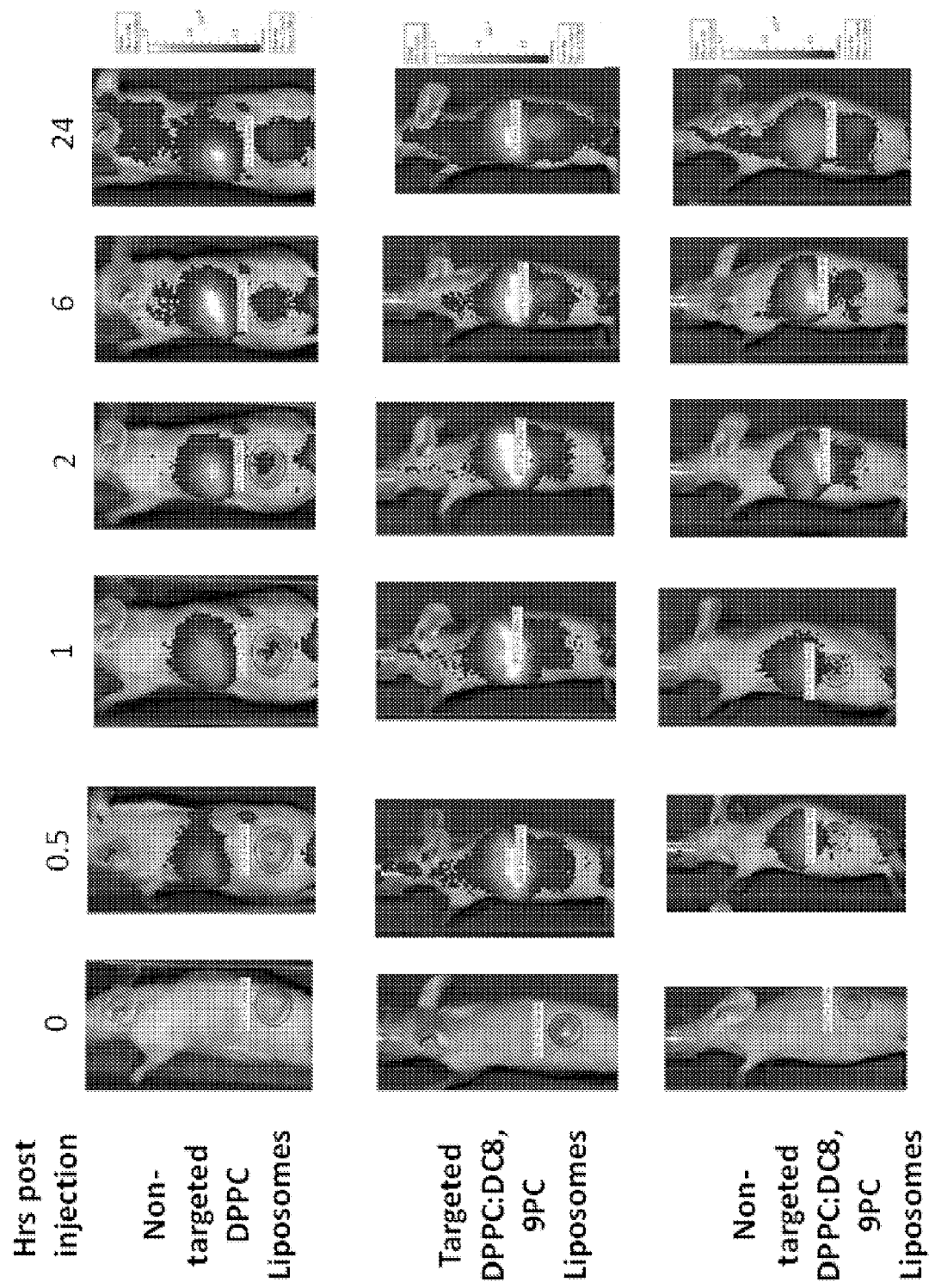
FIG. 14 is a series of fluorescence images illustrating time-dependent uptake of liposomes in KB xenograft-bearing mice. The liposome formulation is DPPC:$DC_{8,9}$PC:DSPE-PEG2000 loaded with doxorubicin.

Athymic nu/nu mice/female were acclimated to a folate deficient diet (Purina Test Diet 5831) for two weeks prior to commencing xenograft development and maintained on the folate deficient diet throughout the entire study period. Animals were weighed, and xenografts were developed by subcutaneously dosing the animal with 6×10$^6$ cells KB (human nasopharyngeal carcinoma) in 100 µL Hanks Balanced Salt Solution in the left flank. Flank tumors were measured every day in two dimensions using vernier calipers, where 'a' was the longest diameter, and 'b' was the shortest diameter. When the tumors reached approximately 10 mm in the longest diameter, the animals were transferred for fluorescent liposome imaging. After tumor development, the KB xenograft-bearing mice were intravenously administered 25 mg liposome/kg body weight of liposomes in a volume of 5 mL/kg by injection via the tail vein. The mice were 7 weeks/20-25 g. There were five mice in each treatment group. Imaging was performed using a Xenogen fluorescent imager. FIG. 14 is a series of fluorescence images illustrating time-dependent uptake of liposomes according to formulations A (lower panel of images), B (middle panel of images), and C (upper panel of images). Over a period of 24 hours, all liposomes were taken up by the liver and the tumor. However, increased tumor uptake was seen with targeted liposomes (DPPC:DC$_{8,9}$PC:DiR:folate, formulation B) as shown in the middle series of images. The results demonstrate that liposomes including DPPC or DPPC/DC$_{8,9}$PC are effectively taken up by the liver and tumor. However, including a targeting molecule, such as folate, may increase tumor-specific uptake.

Example 6

Cytotoxicity Assays

To examine the cytotoxic effects of laser treatment, the loss of luciferase expression and the reduction of cell viability upon laser treatment were evaluated.

Figure 15:
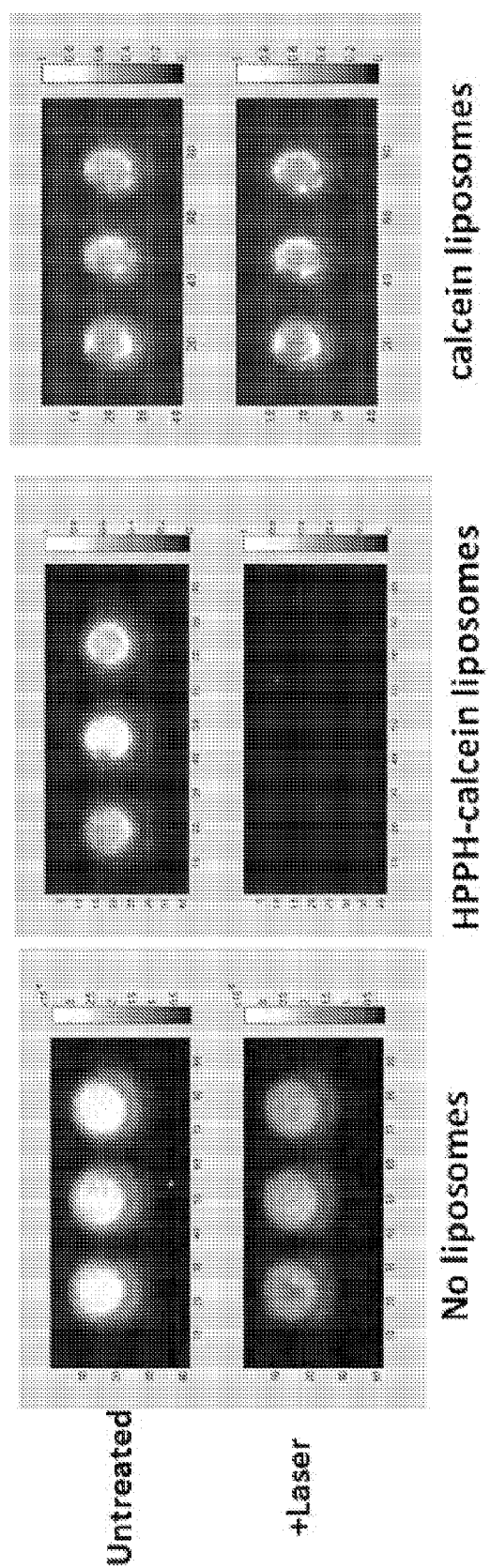
FIG. 15 is a series of fluorescence images illustrating the effect of DPPC:$DC_{8,9}$PC:DSPE-PEG2000 liposomes including HPPH and calcein on luciferase expression in MDA-MB-231LM2$^{Luc+}$ cells when irradiated with a 658-nm laser.

MDA-MB-231LM2$^{Luc+}$ cells plated on 96-well clusters were incubated with liposomes (DPPC:DC$_{8,9}$PC:DSPE-PEG2000 (Formulation I) with HPPH and calcein) for 30 minutes at 37° C. (in triplicate). Subsequently, liposome-cell mixtures were treated with a 658-nm laser for 5 minutes (60 mW). Control samples included cells without liposomes (plus laser treatment) and cell-liposome mixtures not treated with the laser. Luciferase expression was monitored by imaging. As shown in FIG. 15, only liposomes that included both HPPH and calcein effectively eliminated luciferase activity. Liposomes without HPPH were not cytotoxic, and the cells maintained luciferase activity. Additionally, liposomes including HPPH and calcein were not cytotoxic in the absence of laser irradiation.

Figure 16:
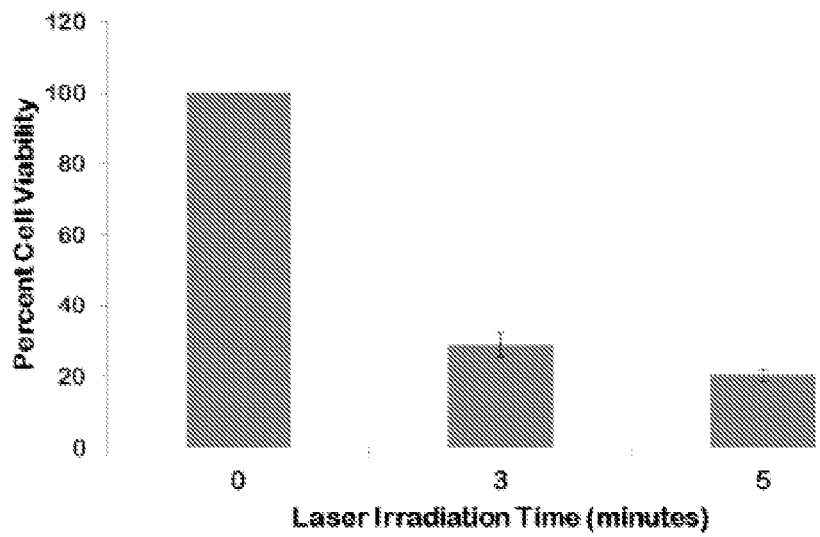
FIG. 16 is a graph illustrating the effect of irradiation for 0-5 minutes with a 660 nm laser on MDA-MB231 cell viability. Prior to irradiation, the cells were incubated for 1 hour with liposomes including DPPC:$DC_{8,9}$PC:DSPE-PEG2000 (Formulation I) with HPPH. Cell viability was assessed 48 hours after irradiation.

MDA-MB231 (*Homo sapiens* mammary gland) cells were incubated in suspension for 1 hour with 5 nmol liposomes (DPPC:DC$_{8,9}$PC:DSPE-PEG2000 (Formulation I) with HPPH) and then treated with a 660 nm laser (90 mW, 1 mm diameter) for 0-5 minutes. The cells were incubated for an additional 48 hours, and viability was assessed using a CellTiterBlue® assay (Promega Corporation, Madison, Wis.). As shown in FIG. 16, irradiation for 3 minutes reduced cell viability by ~70%, and irradiation for 5 minutes reduced cell viability by ~80%. Cytotoxicity was induced by reactive oxygen species generated upon photoactivation of HPPH.

Example 7

Figure 17:
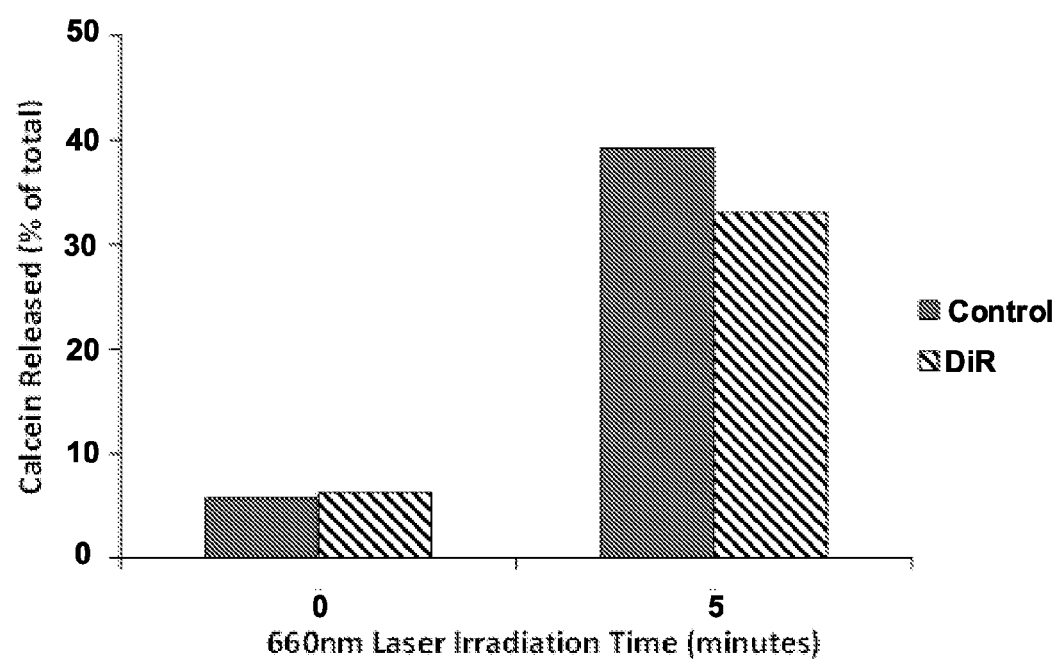
FIG. 17 is a graph illustrating the effect of DiR (1,1'-dioctadecyltetramethyl indotricarbocyanine iodide) incorporation on 660 nm laser-mediated calcein release from liposomes including DPPC:$DC_{8,9}$PC:DSPE-PEG2000 with a mole ratio of 86:10:4. Solid bars represent liposomes without DiR (Formulation I), and diagonal bars represent liposomes with 0.5 mol % DiR (Formulation V).

Bio-Distribution and Tumor Accumulation of DPPC:$DC_{8,9}PC$:HPPH Liposomes in Mice The effect of DiR incorporation on laser-triggered release from liposomes was evaluated. Liposomes were prepared without DiR (Formula I, Table 1) and with 0.5 mol % DiR (Formula V, Table 1). A 150 μL aliquot of liposomes was irradiated for 5 minutes with a 660 nm laser, and the calcein release was measured. The results are shown in FIG. 17. Solid bars represent liposomes without DiR (Formulation I), and diagonal bars represent liposomes with DiR (Formulation V). Bio-distribution studies were performed to determine the optimal time point for in vivo photo-triggering after systemic delivery of liposomes including 0.5 mol % DiR (Formulations V, VI—Table 1). Tumors were grown in mice, and the mice subsequently were injected with liposomes as described in the Methods section. The results demonstrated that DiR does not negatively affect photoactivation of the liposomes.

Figure 18A:
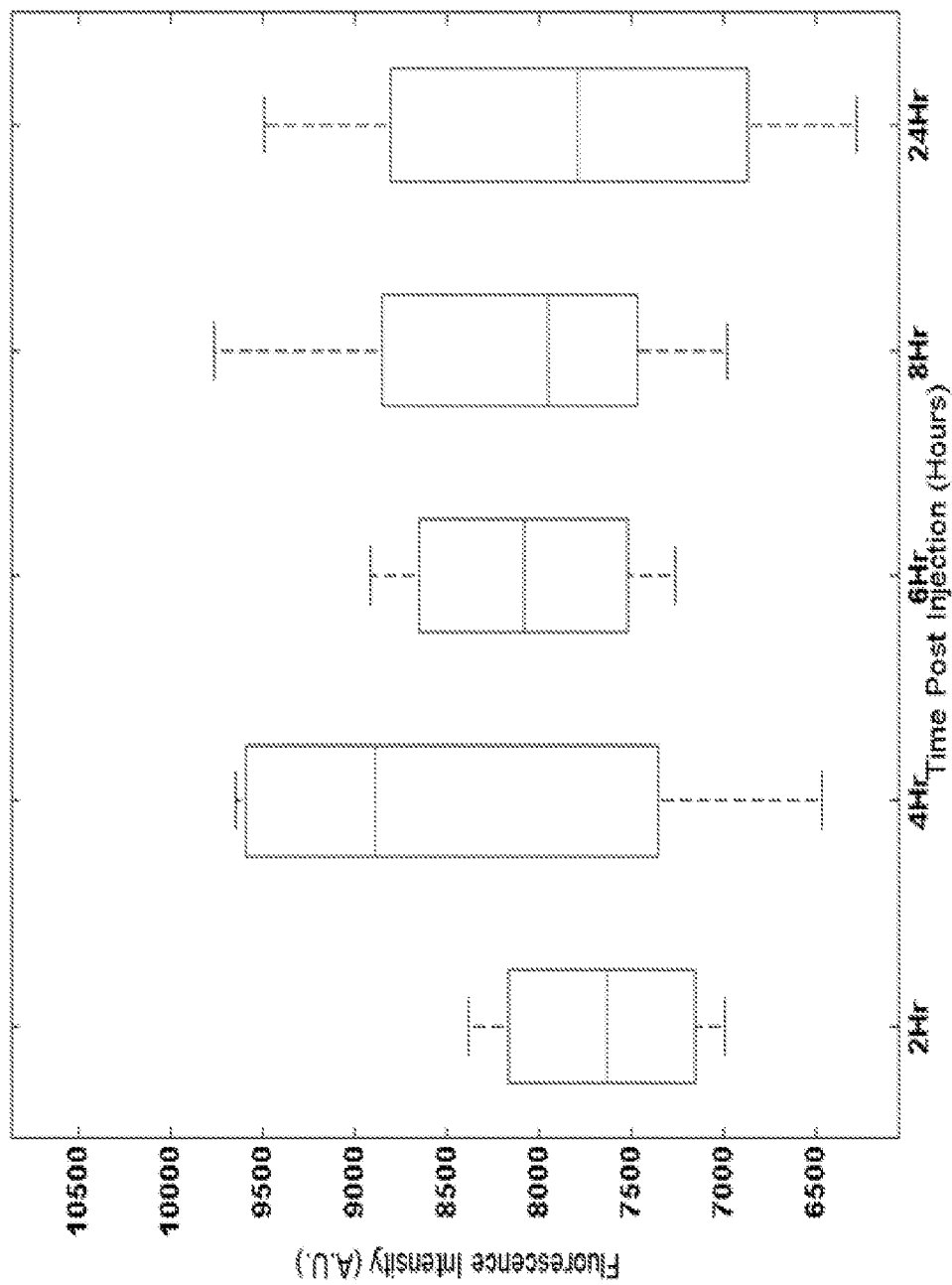
FIG. 18A is a graph of DiR fluorescence intensity versus time, illustrating the time-dependent accumulation of liposomes (Formulation V) in a mouse tumor region of interest (ROI).

The DiR fluorescence signal was treated as a surrogate measurement for liposome accumulation in tumors. DiR fluorescence images were obtained at 2,4,6,8, and 24 hours post tail vein injection of liposomes (FIG. 18B); the tumor region of interest (ROI) is outlined with white circles in the images. The images were analyzed, and the fluorescence intensity counts in the tumor ROI were quantified (FIG. 18A). Maximum tumor fluorescence intensity was observed at 4 hours. However, statistically significant difference in tumor fluorescence intensities at the imaged time-points was not observed, which indicated long circulation time of liposomes. A timeframe of 4-6 hours was determined to be a suitable time interval post injection for photo-triggering.

Example 8

Photo-Triggered Calcein Release in Mouse Tumors

Photo-triggered release of calcein was evaluated. Tumors were grown in mice, and the mice subsequently were injected with liposomes as described in the Methods section. Laser treatment was performed 4 hours post injection as described in Methods section.

Figure 20:
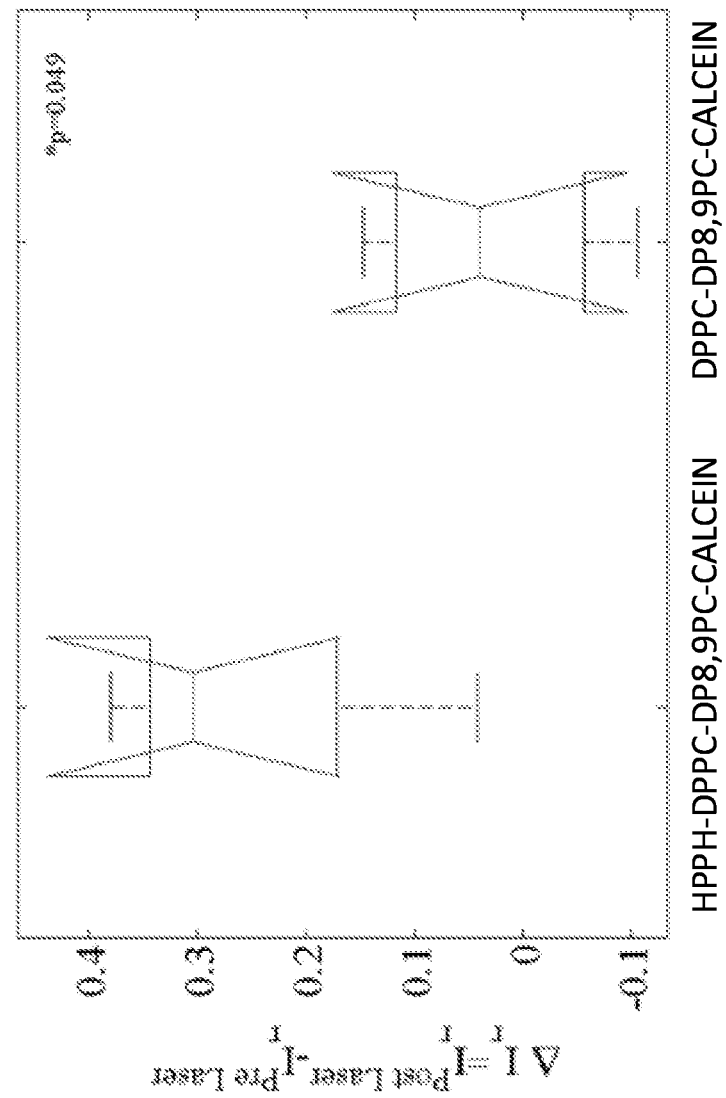
FIG. 20 is a graph showing the differential change in calcein fluorescence intensity ratio between the laser treated and non-treated tumors for the HPPH-DPPC-$DC_{8,9}$PC-calcein (Formulation V) and DPPC-$DC_{8,9}$PC-calcein (Formulation VI) liposome injected mice of FIG. 19.

The fluorescence intensities at calcein emission wavelengths were quantitated for the laser-treated and non-treated tumors in each mouse in both the HPPH-DPPC-$DC_{8,9}$PC-calcein (Formulation V) and the DPPC-$DC_{8,9}$PC-calcein (Formulation VI) treated groups. In FIGS. 19A-19D, the calcein fluorescence images in the tumor regions are overlaid on the white light images for spatial registration. The calcein fluorescence images were normalized with the average pre-laser treatment intensity in the tumor ROI, to enable the quantitation of any increase in fluorescence signal post laser treatment. A clear increase in the calcein fluorescence for laser-treated tumors in HPPH-DPPC-$DC_{8,9}$PC-calcein liposome injected mice was observed, while no such increase was observed in non-laser treated tumors, or in mice injected with DPPC-$DC_{8,9}$PC-calcein liposomes. This result confirmed the wavelength-sensitive nature of release from liposomes. For further quantitation, the differential change in fluorescence intensity ratio of the laser treated to non-treated tumors, pre and post laser treatment was compared (FIG. 20). Approximately 25% greater enhancement in calcein fluorescence intensity ratios was observed for the HPPH-DPPC-$DC_{8,9}$PC-calcein liposome treated mice. (p*=0.049).

Example 9

Tumor Regression

Tumors were grown in mice, and the mice subsequently were injected with liposomes as described in the Methods section. The tumors then were treated with a 660 nm laser and bioluminescence images were obtained as described in the Methods section. For each bioluminescence image, mice were injected with D-luciferin 20 minutes prior to image acquisition.

Figure 22A:
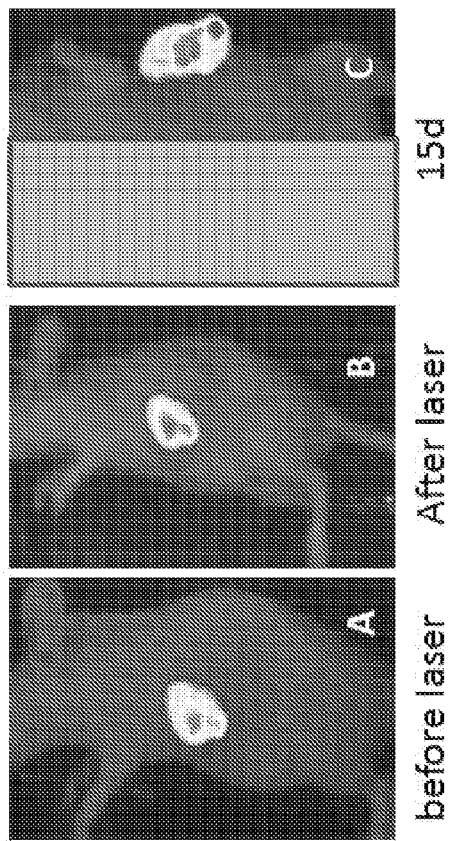
FIGS. 22A and 22B are a series of bioluminescent images of luciferin expression in tumors in a mouse injected with DPPC-$DC_{8,9}$PC-calcein liposomes (Formulation VI). Images were obtained pre-treatment and post-treatment at 0 days, and 15 days. The tumor on the mouse's left side was treated with a laser (22A); the tumor on the mouse's right side was not treated with the laser (22B). The images at 0 days are side views; the images at 15 days are ventral views.
Figure 22B:
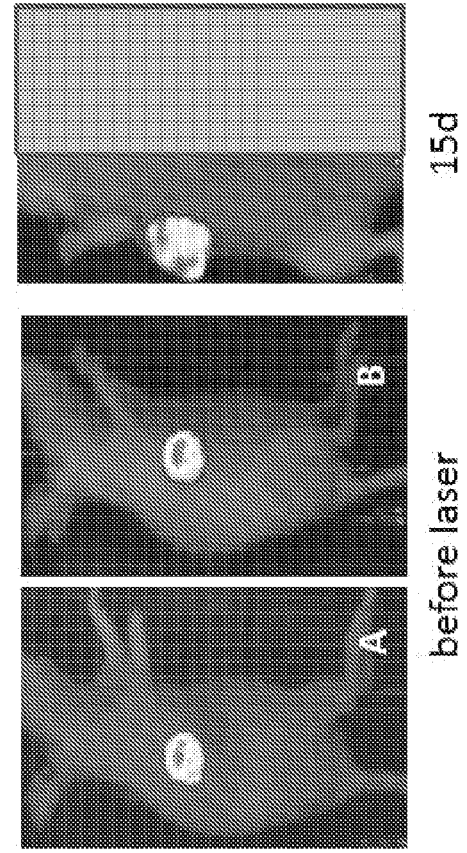
Figure 23:
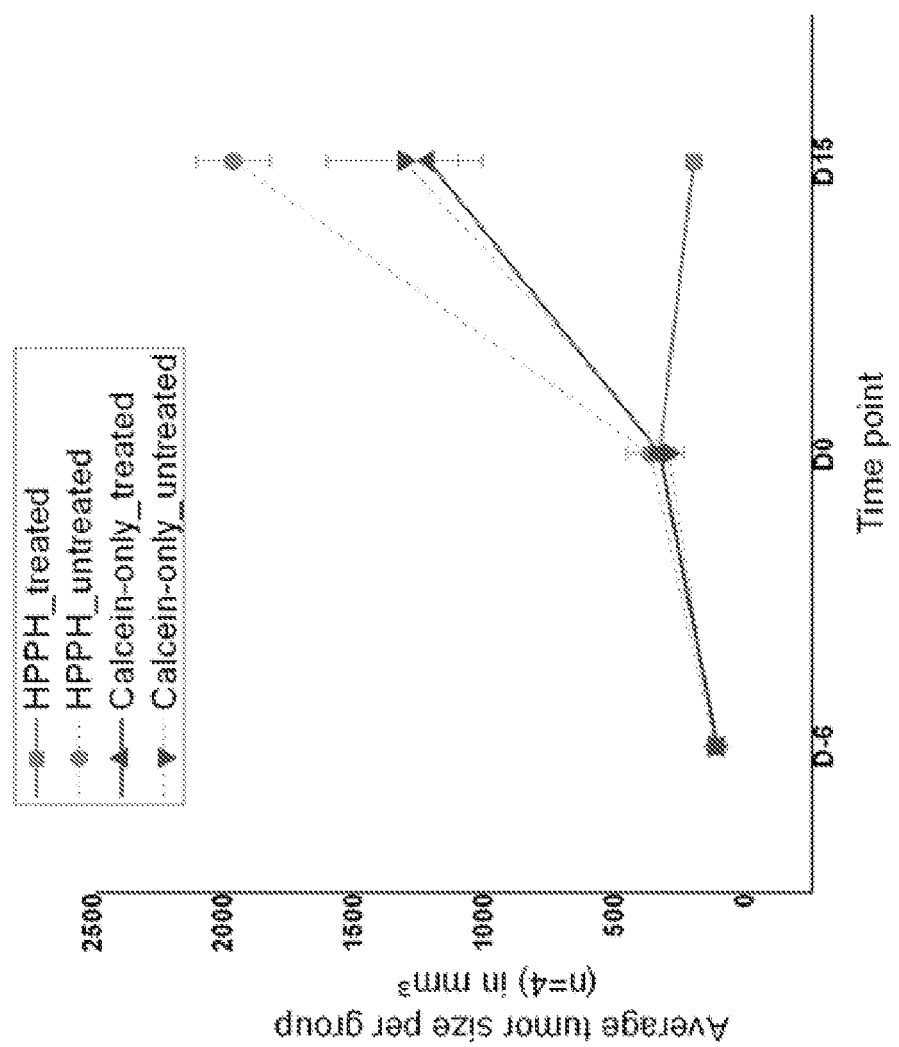
FIG. 23 is a graph of average tumor size versus time illustrating tumor regression after injection with (1) HPPH-DPPC-$DC_{8,9}$PC-calcein liposomes (Formulation V) and laser treatment (squares), (2) HPPH-DPPC-$DC_{8,9}$PC-calcein liposomes (Formulation V) and no laser treatment (circles), (3) DPPC-$DC_{8,9}$PC-calcein liposomes (Formulation VI) and laser treatment (triangles), and (4) DPPC-$DC_{8,9}$PC-calcein liposomes (Formulation VI) and no laser treatment (inverted triangles).

Mice were observed for 15 days post laser treatment, and tumor growth was followed both with bioluminescence imaging and caliper-based measurements of tumor size on day 4, 8, and 15. As shown in FIGS. 21A and 21B, laser-treated tumors in HPPH-DPPC-$DC_{8,9}$PC-calcein (Formulation V) injected mice exhibited continued reduction in tumor bioluminescence signal, and reduction in tumor volume (FIG. 21A) compared to tumors that were not laser-treated (FIG. 21B). In contrast, laser-treated tumors in DPPC-$DC_{8,9}$PC-calcein (Formulation VI) injected mice did not exhibit reduction in tumor bioluminescence signal and tumor volume (FIG. 22A) compared to tumors that were not laser-treated (FIG. 22B). The results are illustrated graphically in FIG. 23. The data is averaged per group (n=4). Data was obtained six days prior to liposome injection and laser treatment (D-6), immediately following liposome injection and laser treatment (D0), and 15 days after liposome injection and laser treatment (D15). As shown in FIG. 23, tumor regression was observed only in mice that received HPPH-DPPC-calcein liposomes and laser treatment.

Mice were sacrificed, and the xenografts were excised and preserved 15 days after laser treatment. Xenografts were fixed, sectioned, and stained as described in the Methods section. Histopathology data is shown in FIG. 24 for two mice that received HPPH-DPPC-$DC_{8,9}$PC-calcein liposomes and laser treatment (animals 1 and 2) and one mouse that received DPPC-calcein liposomes and laser treatment (animal 3). Tumor size reduction was evident only in the mice that received HPPH-DPPC-$DC_{8,9}$PC-calcein liposomes and laser treatment. FIG. 25A (low magnification) and 25B (higher magnification) show evidence of tumor necrosis after injection with HPPH-DPPC-$DC_{8,9}$PC-calcein liposomes (Formulation V) and laser treatment.

This tumor viability reduction was not observed in the DPPC-$DC_{8,9}$PC-calcein liposomes injected mice, or in non-laser treated tumors in HPPH-DPPC-$DC_{8,9}$PC-calcein injected mice. These observations confirmed that therapy was due to photo-activation of HPPH drug and not due to a photo-thermal effect, providing further evidence for wavelength-specific light-triggered collapse of HPPH-DPPC-$DC_{8,9}$PC-calcein liposomes.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A photoactivatable lipid-based nanoparticle, comprising:
a vesicle wall surrounding a cavity, the vesicle wall comprising
(i) a lipid bilayer comprising
(a) from 10 mol % to 20 mol % 1,2-bis(tricosa-10,12-diynoyl)-sn-glycero-3-phosphocholine (DC$_{8,9}$PC),
(b) from 3 mol % to 5 mol % 1,2-distearoyl-sn-glycero-3-phosphoethanolamine-N-methoxy (polyethylene glycol) (DSPE-PEG), and
(c) dipalmitoylphosphatidylcholine (DPPC), and
(ii) 2-[1-hexyloxyethyl]-2-devinyl pyropheophorbide-a (HPPH) within the lipid bilayer,
wherein the vesicle wall has a lipid:HPPH weight ratio from 80:1 to 10:1, and wherein the lipid bilayer is destabilized by targeted application of light having a wavelength of 650-670 nm and a selected intensity for an effective period of time.

2. The photoactivatable lipid-based nanoparticle of claim 1, wherein the lipid bilayer comprises one or more segregated regions of DC$_{8,9}$PC and the HPPH is preferentially located within the one or more segregated regions of DC$_{8,9}$PC.

3. The photoactivatable lipid-based nanoparticle of claim 1, wherein the nanoparticle has a diameter from 80 nm to 200 nm.

4. The photoactivatable lipid-based nanoparticle of claim 1, further comprising at least one agent within the cavity.

5. The photoactivatable lipid-based nanoparticle of claim 4, wherein the agent is an anti-cancer agent, an imaging agent, or an anti-inflammatory agent.

6. The photoactivatable lipid-based nanoparticle of claim 5, wherein the agent is an anti-cancer agent.

7. The photoactivatable lipid-based nanoparticle of claim 6, wherein the agent is topotecan.

8. A pharmaceutical composition comprising a photoactivatable lipid-based nanoparticle according to claim 1 and a pharmaceutically acceptable carrier.

9. The method of claim 1, wherein the lipid bilayer comprises 76-86 mol % DPPC.

10. A method for delivering an agent from a photoactivatable lipid-based nanoparticle, the method comprising:
providing a photoactivatable lipid-based nanoparticle according to claim 4; and
subsequently irradiating the photoactivatable lipid-based nanoparticle with targeted application of light having a wavelength of 650-670 nm and a selected intensity for an effective period of time to activate at least a portion of the HPPH and release at least a portion of the agent from the cavity of the photoactivatable lipid-based nanoparticle.

11. The method of claim 10, wherein irradiating the photoactivatable lipid-based nanoparticle with targeted application of light comprises irradiating the photoactivatable lipid-based nanoparticle with a laser that produces the light having a wavelength of 650-670 nm.

12. The method of claim 10, wherein:
(a) the selected intensity is from 1 mW to 500 mW;
(b) the effective period of time is at least 30 seconds; or
(c) both (a) and (b).

13. The method of claim 10, wherein the agent is a bioactive agent, the method further comprising:
identifying a subject as having a condition that may be treated with HPPH, the bioactive agent, or both HPPH and the bioactive agent;
administering the photoactivatable lipid-based nanoparticle to the subject; and
subsequently irradiating the photoactivatable lipid-based nanoparticle by targeted application of light having a wavelength of 650-670 nm and a selected intensity to a targeted portion of the subject for the effective period of time.

14. The method of claim 13, wherein the subject has a tumor and the targeted portion of the subject includes an area proximate a location of the tumor.

15. The method of claim 14, wherein administering the photoactivatable lipid-based nanoparticle to the subject comprises administering an amount of the photoactivatable lipid-based nanoparticle effective to induce tumor size regression.

16. The method of claim 13, wherein irradiating is performed 4-6 hours after administering the photoactivatable lipid-based nanoparticle to the subject.

17. The method of claim 13, wherein administering the photoactivatable lipid-based nanoparticle to the subject comprises intravenously injecting the photoactivatable lipid-based nanoparticle into the subject.

18. The method of claim 13, wherein administering the photoactivatable lipid-based nanoparticle to the subject comprises administering a pharmaceutical composition comprising the photoactivatable lipid-based nanoparticle to the subject.

19. The method of claim 13, wherein subsequently irradiating the photoactivatable lipid-based nanoparticle by targeted application of light comprises:
externally applying the light to the targeted portion of the subject for the effective period of time, thereby transcutaneously applying the light to the tumor; or
internally applying the light to the targeted portion of the subject for the effective period of time.

20. The method of claim 13, wherein the bioactive agent is an anti-cancer agent.

21. The method of claim 20, wherein the anti-cancer agent is topotecan.

* * * * *

UNITED STATES PATENT AND TRADEMARK OFFICE
CERTIFICATE OF CORRECTION

PATENT NO. : 10,117,942 B2
APPLICATION NO. : 14/904385
DATED : November 6, 2018
INVENTOR(S) : Puri et al.

Page 1 of 1

It is certified that error appears in the above-identified patent and that said Letters Patent is hereby corrected as shown below:

In the Claims

In Claim 9, at Column 29, Line 40, "The method of claim 1" should read --The photoactivated lipid-based nanoparticle of claim 1,--

Signed and Sealed this
Third Day of September, 2019

Andrei Iancu
*Director of the United States Patent and Trademark Office*